(12) United States Patent
Stern et al.

(10) Patent No.: US 8,133,505 B2
(45) Date of Patent: *Mar. 13, 2012

(54) TRANSDERMAL DELIVERY SYSTEM FOR DRIED PARTICULATE OR LYOPHILIZED MEDICATIONS

(75) Inventors: Meir Stern, Rehovot (IL); Galit Levin, Nordiya (IL)

(73) Assignee: TransPharma Medical Ltd., Lod (IL)

( * ) Notice: Subject to any disclaimer, the term of this patent is extended or adjusted under 35 U.S.C. 154(b) by 460 days.

This patent is subject to a terminal disclaimer.

(21) Appl. No.: 12/357,283

(22) Filed: Jan. 21, 2009

(65) Prior Publication Data

US 2009/0137480 A1 May 28, 2009

Related U.S. Application Data

(63) Continuation-in-part of application No. 11/582,920, filed on Oct. 17, 2006, now Pat. No. 7,662,404, which is a continuation-in-part of application No. 10/699,582, filed on Oct. 31, 2003, now Pat. No. 7,335,377.

(30) Foreign Application Priority Data

Oct. 31, 2002 (IL) ............................................ 152574

(51) Int. Cl.
  *A61K 38/23* (2006.01)
  *A61K 9/70* (2006.01)
  *C07K 14/585* (2006.01)
  *A61L 15/16* (2006.01)
  *A61F 13/02* (2006.01)

(52) U.S. Cl. ........ 424/447; 424/449; 530/307; 514/11.9; 427/2.31

(58) Field of Classification Search .................. None
  See application file for complete search history.

(56) References Cited

U.S. PATENT DOCUMENTS

| | | | |
|---|---|---|---|
| 3,964,482 A | 6/1976 | Gerstel et al. ................. 128/260 |
| 4,304,692 A | 12/1981 | Hughes et al. ............. 525/54.11 |
| 4,597,900 A | 7/1986 | Orlowski et al. ............. 530/307 |
| 4,711,781 A | 12/1987 | Nick .............................. 424/446 |
| 4,915,950 A | 4/1990 | Miranda et al. ............... 424/448 |
| 5,019,034 A | 5/1991 | Weaver et al. ................. 604/20 |
| 5,158,537 A | 10/1992 | Haak et al. ..................... 604/20 |
| H1160 H | 4/1993 | Maulding et al. ............... 604/20 |
| 5,230,898 A | 7/1993 | Horstmann et al. .......... 424/449 |
| 5,445,609 A | 8/1995 | Lattin et al. .................... 604/20 |
| 5,611,806 A | 3/1997 | Jang .............................. 606/167 |
| 5,618,265 A | 4/1997 | Myers et al. .................... 604/20 |
| 5,681,580 A | 10/1997 | Jang et al. .................... 424/449 |
| 5,685,837 A | 11/1997 | Horstmann ...................... 604/20 |
| 5,807,306 A | 9/1998 | Shapland et al. ............... 604/21 |
| 5,885,211 A | 3/1999 | Eppstein et al. .............. 600/309 |
| 5,928,571 A | 7/1999 | Chan .............................. 252/514 |
| 5,944,685 A | 8/1999 | Muroki ........................... 604/20 |
| 5,958,447 A | 9/1999 | Haralambopoulos et al. .............................. 424/449 |
| 5,983,130 A | 11/1999 | Phipps et al. .................... 604/20 |
| 5,983,135 A | 11/1999 | Avrahami ........................ 604/20 |
| 6,002,961 A | 12/1999 | Mitragotri et al. .............. 604/20 |
| 6,022,316 A | 2/2000 | Eppstein et al. .............. 600/309 |
| 6,050,988 A | 4/2000 | Zuck .......................... 604/890.1 |
| 6,083,196 A | 7/2000 | Trautman et al. ............... 604/46 |
| 6,142,939 A | 11/2000 | Eppstein et al. .............. 600/309 |
| 6,148,232 A | 11/2000 | Avrahami ........................ 604/20 |
| 6,169,920 B1 | 1/2001 | Haak et al. ....................... 604/20 |
| 6,173,202 B1 | 1/2001 | Eppstein ........................ 604/20 |
| 6,219,577 B1 | 4/2001 | Brown, III et al. ............. 604/20 |
| 6,274,166 B1 | 8/2001 | Sintov et al. .................. 424/449 |
| 6,274,582 B1 | 8/2001 | Marin ........................ 514/254.1 |
| 6,317,629 B1 | 11/2001 | Haak et al. ....................... 604/20 |
| 6,328,033 B1 | 12/2001 | Avrahami ................ 128/203.15 |
| 6,335,030 B1 | 1/2002 | Hoeck et al. .................. 424/449 |
| 6,522,918 B1 | 2/2003 | Crisp et al. ...................... 604/20 |
| 6,526,316 B2 | 2/2003 | Iga et al. ......................... 604/20 |
| 6,597,946 B2 | 7/2003 | Avrahami et al. ............... 604/20 |
| 6,611,706 B2 | 8/2003 | Avrahami et al. ............... 604/20 |
| 6,615,079 B1 | 9/2003 | Avrahami ........................ 604/20 |
| 6,622,037 B2 | 9/2003 | Kasano ........................... 604/20 |
| 6,662,044 B2 | 12/2003 | Crawford et al. ............... 604/20 |
| 6,708,060 B1 | 3/2004 | Avrahami et al. ............... 604/20 |
| 6,711,435 B2 | 3/2004 | Avrahami ........................ 604/20 |
| 7,062,317 B2 | 6/2006 | Avrahami et al. ............... 604/20 |
| 7,123,957 B2 | 10/2006 | Avrahami ........................ 604/20 |
| 7,164,942 B2 | 1/2007 | Avrahami et al. ............... 604/20 |
| 7,335,377 B2 | 2/2008 | Stern et al. .................... 424/447 |
| 7,662,404 B2 | 2/2010 | Stern et al. .................... 424/447 |
| 2002/0010414 A1 | 1/2002 | Coston et al. .................. 606/20 |

(Continued)

FOREIGN PATENT DOCUMENTS

EP  0391172  3/1990

(Continued)

OTHER PUBLICATIONS

Saran Kumar et al., In vivo transdermal iontophoretic delivery of growth hormone releasing factor GRF (1-44) in hairless guinea pigs, Elsevier Science, Journal of Controlled Release, vol. 18, pp. 213-220 (1992).

David T.-W. Lau et al., Effect of Current Magnitude and Drug Concentration on Iontophoretic Delivery of Octreotide Acetate (Sandostatin®) in the Rabbit, Pharmaceutical Research, vol. 11, No. 12, pp. 1742-1746 (1994).

P. Singh et al., Modelling of plasma levels of drugs following transdermal iontophoresis, Journal of Controlled Release, Elsevier Science, vol. 33, pp. 293-298 (1995).

(Continued)

*Primary Examiner* — Marsha Tsay

(74) *Attorney, Agent, or Firm* — Winston & Strawn LLP

(57) ABSTRACT

The present invention provides a system for transdermal delivery of dried or lyophilized pharmaceutical compositions and methods using thereof. The system comprises an apparatus for facilitating transdermal delivery of an agent that generates hydrophilic micro-channels, and a patch comprising a therapeutically active agent. The present invention is useful for transdermal delivery of hydrophilic agents, particularly of high molecular weight proteins.

22 Claims, 15 Drawing Sheets

U.S. PATENT DOCUMENTS

| | | | |
|---|---|---|---|
| 2002/0038101 A1 | 3/2002 | Avrahami et al. | 606/20 |
| 2002/0058936 A1 | 5/2002 | Avrahami et al. | 606/41 |
| 2003/0139731 A1 | 7/2003 | Marchitto et al. | 604/890.1 |
| 2003/0204163 A1 | 10/2003 | Marchitto et al. | 604/65 |
| 2004/0059282 A1 | 3/2004 | Flock et al. | 604/20 |
| 2005/0119605 A1 | 6/2005 | Sohn | 604/21 |

FOREIGN PATENT DOCUMENTS

| | | |
|---|---|---|
| EP | 0413487 | 2/1991 |
| EP | 0912239 B1 | 9/2001 |
| JP | 03081217 | 4/1991 |
| JP | 05103838 | 4/1993 |
| JP | 08211053 | 8/1996 |
| WO | WO 97/07734 | 3/1997 |
| WO | WO 97/48485 | 12/1997 |
| WO | WO 98/08492 | 3/1998 |
| WO | WO 00/27473 | 5/2000 |
| WO | WO 00/27473 A1 | 5/2000 |
| WO | WO 00/38781 | 7/2000 |
| WO | WO 01/07096 A1 | 2/2001 |
| WO | WO 02/060418 A1 | 8/2002 |
| WO | WO 02/085451 A2 | 10/2002 |
| WO | WO 02/092163 A2 | 10/2002 |
| WO | WO 02/091934 A2 | 11/2002 |
| WO | WO 03/039620 A2 | 5/2003 |
| WO | WO 03/089043 A2 | 10/2003 |
| WO | WO 2006/131931 A2 | 12/2006 |

OTHER PUBLICATIONS

Harma Ellens et al., Transdermal iontophoretic delivery of [$^3$H]GHRP in rats, International Journal of Pharmaceutics, vol. 159, pp. 1-11 (1997).

Yuri A. Chizmadzhev et al., Electrical Properties of Skin at Moderate Voltages: Contribution of Appendageal Macropores, Biophysical Journal, vol. 74, pp. 843-856 (1998).

Sintov et al., Radiofrequency-driven skin microchanneling as a new way for electrically assisted transdermal delivery of hydrophilic drugs, Journal of Controlled Release 89: 311-320 (2003).

Breimer et al., Peptides from the calcitonin genes: molecular genetics, structure and function, Biochem. J. 255: 377-390, 1988.

Pless et al., Nature New Biol. 240: 62-63, 1972.

Jansz et al., Identification of a new calcitonin gene in the salmon *Oncorhynchus gorbuscha,* Proc. Natl. Acad. Sci. U.S.A. 93: 12344-12348, 1996.

Katafuchi et al., Calcitonin Receptor-stimulating Peptide, a New Member of the Calcitonin Gene-related Peptide Family, J. Biol. Chem. 278: 12046-12054, 2003.

European Pharmacopoeia, $4^{th}$ edition, 2002. Somatropin 01/2002:0951, p. 1937-1939.

Supplementary European Search Report, Application No. EP 03769877, dated Feb. 17, 2011.

U.S. Appl. No. 10/699,582 Requirement for Restriction /Election dated May 1, 2006.

U.S. Appl. No. 10/699,582 Non Final Rejection dated Jul. 24, 2006.

U.S. Appl. No. 10/699,582 Final Rejection dated Dec. 26, 2006.

U.S. Appl. No. 10/699,582 Advisory Action dated Mar. 14, 2007.

U.S. Appl. No. 10/699,582 Non Final Rejection May 25, 2007.

U.S. Appl. No. 11/327,016 Requirement for Restriction /Election dated Nov. 21, 2006.

U.S. Appl. No. 11/327,016 Non Final Rejection dated Jan. 23, 2007.

U.S. Appl. No. 11/327,016 Final Rejection dated Jun. 25, 2007.

U.S. Appl. No. 11/327,016 Advisory Action dated Aug. 31, 2007.

U.S. Appl. No. 11/390,844 Requirement for Restriction /Election dated Jul. 11, 2007.

U.S. Appl. No. 11/390,844 Non Final Rejection dated Sep. 4, 2007.

U.S. Appl. No. 11/582,920 Requirement for Restriction /Election dated Nov. 19, 2008.

U.S. Appl. No. 11/582,920 Non Final Rejection dated Mar. 9, 2009.

TRANSDERMAL DELIVERY SYSTEM FOR DRIED PARTICULATE OR LYOPHILIZED MEDICATIONS

CROSS-REFERENCES TO RELATED APPLICATIONS

The present invention is a Continuation-in-part of U.S. patent application Ser. No. 11/582,920 filed on Oct. 17, 2006, now U.S. Pat. No. 7,662,404 which is a Continuation-in-part of U.S. patent application Ser. No. 10/699,582 filed on Oct. 31, 2003, now U.S. Pat. No. 7,335,377, which claims the benefit of Israel Patent Application No. IL 152574 filed on Oct. 31, 2002, the contents of each of which are incorporated herein by reference thereto.

FIELD OF THE INVENTION

The present invention relates generally to the field of drug formulations for use in conjunction with a transdermal delivery apparatus and relates specifically to a drug-containing matrix that is useful as a component in a transdermal system for effective transdermal delivery of dried or lyophilized medications, in conjunction with an apparatus that operates by forming channels in the skin of a subject.

BACKGROUND OF THE INVENTION

There are clearly many theoretical advantages to the transdermal delivery of dried or lyophilized drugs instead of commercially available oral or injectable forms of these drugs. Delivery of a drug across the skin of a patient obviates the problems of drug inactivation by gastrointestinal fluids or enzymes, fluctuations in absorption from the gastrointestinal tract, and hepatic first pass inactivation, while also avoiding the inconvenience of injection. However, hitherto proposed devices or methods for transdermal delivery of dried particulate or lyophilized drug agents have not successfully yielded reliable uptake and sustained serum levels of the active agent.

Generally speaking the objective of transdermal drug delivery has been tackled using one of two complementary approaches known in the art. One approach provides formulations of drugs that may be applied to the skin in the form of patches, films or matrices of varying compositions, and the alternative approach utilizes a method of puncturing the skin or otherwise disrupting the impermeable layers of the skin to facilitate the entry of drugs into the systemic circulation.

Transdermal Patches

Patches or matrices almost invariably comprise some type of penetration enhancer and some type of adhesive layer, and are known to cause irritation or edema and to produce non-uniform rates and levels of drug uptake among different patients and different skin types.

There are two prevalent types of transdermal patch design, namely the reservoir type where the drug is contained within a reservoir having a basal surface that is permeable to the drug, and a matrix type, where the drug is dispersed in a polymer layer affixed to the skin. Both types of device also typically include a backing layer and an inner release liner layer that is removed prior to use.

EP 0391172 describes a transdermal patch having a matrix composed of a water-insoluble material that contains islands of solid particles of drug in a water-soluble/swellable polymer and an underlayer that controls the amount of water vapor passing from the skin to the matrix. The matrix is said to be activated by water vapor from the skin.

Compositions or devices in the form of specific types of patches adapted for the transdermal delivery of dry powder or lyophilized drugs have been disclosed for example in EP 0912239 B1 to PowderJect Research Ltd. that discloses "Method for providing dense particle compositions for use in transdermal particle delivery".

Methods for transdermal delivery of powders are also disclosed in U.S. Pat. No. 5,983,135 to Avrahami.

U.S. Pat. No. 4,915,950 to Miranda et al. discloses a method for making a transdermal delivery device comprising laminating an adsorbent source layer to a pharmaceutically acceptable contact adhesive layer, the contact adhesive layer comprised of a material that is permeable to the drug, printing a drug in liquid form onto the adsorbent layer, laminating an anchor adhesive layer to the source layer, and applying a backing layer to the anchor adhesive layer.

Methods for transdermal delivery of Growth Hormone Releasing Peptide (GHRP) are disclosed in WO 98/08492 to Novo Nordisk. Methods for transdermal delivery of growth hormone releasing peptide in conjunction with iontophoresis are also disclosed in scientific publications by Singh et al. (J. Controlled Release, 33, 293-298, 1995); Lau et al. (Pharmaceutical Research 11, 1742-1746, 1994); Kumar et al. (J. Controlled Release 18, 213-220, 1992); Ellens et al. (Int. J. Pharm. 159, 1-11, 1997). In those publications, the onset of the electrical current induces the influx of GHRP across the skin, and cessation of the current terminates the influx of the peptide.

Transdermal Delivery Apparatus

Electrotransport or iontophoretic drug delivery devices have also been disclosed as being useful for the delivery of dried or lyophilized drugs for which it is anticipated that transdermal delivery would be advantageous. U.S. Pat. Nos. 6,169,920 and 6,317,629 to Alza for example disclose iontophoretic drug delivery apparatus, and U.S. Pat. No. 5,983,130 to Alza discloses an electrotransport agent delivery method and apparatus suitable for ionizable drugs.

U.S. Pat. No. 5,681,580 to Jang et al. discloses a patch-like device for iontophoretic transdermal medication of insulin having a container for holding gel-like insulin, and a power supply for furnishing insulin with electricity.

Electroporation is also well known in the art as a method to increase pore size by application of an electric field. Electroporation is disclosed as a means for transiently decreasing the electrical resistance of the stratum corneum and increasing the transdermal flux of small molecules by applying an electric field to increase the size of existing pores (Chizmadzhev et al., Biophysics Journal, 1998, 74(2), 843-856).

U.S. Pat. No. 5,019,034 to Weaver et al. describes apparatus for applying high voltage, short duration electrical pulses on the skin to produce electroporation.

WO 97/07734 to Eppstein et al. discloses thermal ablation of the stratum corneum using an electrically resistive element in contact with the stratum corneum, such that a high current through the element causes a general heating of tissue in its vicinity, most particularly the stratum corneum, the 10-50 micron thick outermost layer of the skin.

U.S. Pat. Nos. 5,885,211, 6,022,316, 6,142,939 and 6,173,202 to Eppstein et al., which are incorporated herein by reference, describe methods for forming micro-pores in the stratum corneum by heating tissue-bound water above the vapor point with a heat-conducting element, so as to enhance transdermal transport of an analyte or active agent. Further enhancement techniques include the use of sonic energy, pressure, and chemical enhancers. For example, U.S. Pat. No. 6,002,961 to Mitragotri et al. discloses a method that includes a simultaneous application of ultrasound and protein on the skin in order to deliver therapeutic doses of proteins across the skin into the blood.

U.S. Pat. No. 3,964,482 to Gerstel, U.S. Pat. No. 6,050,988 to Zuck, and U.S. Pat. No. 6,083,196 to Trautman et al. describe other apparatus and methods for facilitating transdermal delivery of an agent.

U.S. Pat. No. 6,148,232 to Avrahami, which is incorporated herein in its entirety by reference, describes apparatus for applying electrodes at respective points on skin of a subject and applying electrical energy between two or more of the electrodes to cause resistive heating and subsequent ablation of the stratum corneum primarily in an area intermediate the respective points. Various techniques for limiting ablation to the stratum corneum are described, including spacing of the electrodes and monitoring the electrical resistance of skin between adjacent electrodes.

There is thus an unmet need for reliable and safe compositions suitable for transdermal delivery of drugs in dried particulate or lyophilized form. The advantages of this approach would be particularly striking for peptides and polypeptides, as well as for other bioactive agents including oligonucleotides and polynucleotides.

SUMMARY OF THE INVENTION

The present invention relates to an effective system and methods for transdermal delivery of an active dried or lyophilized agent. The present invention relates to an apparatus and methods for ablating the skin and transdermally delivering an active agent packaged in a dried or lyophilized form to the pretreated skin.

Particularly, the present invention relates to apparatus and methods for transdermally delivering an active dried or lyophilized agent using a suitable medical skin patch.

The present invention also relates to a medical skin patch comprising a dried hydrophilic active agent. Particularly, the present invention relates to printed patches and method of preparation thereof, for transdermal delivery of an active dried agent.

The compositions and the methods of the present invention are suitable for use with many of the patches known in the art, though application of the drug with the system of the present invention using a printed patch has proven particularly effective and has yielded unexpectedly advantageous exemplary results.

It is now disclosed for the first time that use of a patch comprising a dried or lyophilized pharmaceutical composition comprising a therapeutically active agent, placed on an area of the skin pretreated by an apparatus that generates micro-channels unexpectedly provides therapeutically effective serum levels of the active agent. The dose efficiency or bioavailability obtained was adequate to provide therapeutic effects in a subject.

These results were totally unexpected due to the fact that usually in transdermal delivery, bioavailability values are low. Moreover, the unexpected results were achieved even for a very large molecule with very poor diffusion coefficient.

In addition, it is disclosed that a patch, and particularly a printed patch, comprising a dried or lyophilized pharmaceutical composition comprising a therapeutically active agent provides stability and long shelf life of the active agent, which is otherwise unstable in solution or suspension.

It is also disclosed that a patch, and particularly a printed patch, comprising a dried or lyophilized pharmaceutical composition comprising a therapeutically active agent provides a means for transdermal delivery of the active agent in a known, accurate and controlled dosage. According to the invention, printing of a pharmaceutical composition comprising a therapeutically active agent on a patch provides uniform and even distribution of the active agent on the printed patch, thereby highly improves transdermal delivery and bioavailability of the active agent as compared to the delivery from a powder patch. This improved transdermal delivery from a printed patch compared to a powder patch is most pronounced when the amount of the active agent applied on the patch is low (up to several hundreds of micrograms).

The principles of the invention are exemplified herein below with human growth hormone, human insulin, salmon calcitonin, and with a fragment of human parathyroid hormone (hPTH) having the amino acid residues 1-34 of the full-length hormone. It is explicitly intended that the compositions and methods comprising the system of the invention are applicable to a wide variety of proteins, polypeptides, peptides, polynucleotides, oligonucleotides, and other bioactive molecules including, but not limited to, growth factors and hormones.

According to a first aspect, the present invention provides a system for transdermal delivery of an active therapeutic agent from a dried pharmaceutical composition comprising: an apparatus for facilitating transdermal delivery of a therapeutically active agent through skin of a subject, said apparatus capable of generating a plurality of micro-channels in an area on the skin of the subject, and a patch comprising at least one therapeutically active agent in a dried pharmaceutical composition.

The term "micro-channel" as used throughout the specification and claims refers to a hydrophilic pathway generally extending from the surface of the skin through all or a significant part of the stratum corneum, through which pathway molecules can diffuse. The patch is placed over the treated region in which the micro-channels are present.

According to one currently preferred embodiment of the invention, the system comprises an apparatus for facilitating transdermal delivery of an active agent through the skin of a subject, said apparatus comprising:
a. an electrode cartridge, optionally removable, comprising a plurality of electrodes; and
b. a main unit comprising a control unit which is adapted to apply electrical energy to the plurality of electrodes when the plurality of electrodes are in vicinity of the skin, typically generating current flow or one or more sparks, enabling ablation of stratum corneum in an area beneath said plurality of electrodes, thereby generating a plurality of micro-channels.

According to another embodiment, the control unit of the apparatus comprises circuitry to control the magnitude, frequency, and/or duration of the electrical energy delivered to the plurality of electrodes, so as to control the current flow or spark generation, and thus the width, depth and shape of the plurality of micro-channels. Preferably, the electrical energy is at radio frequency.

In a currently preferred embodiment, the electrode cartridge of the apparatus comprising the plurality of electrodes enables generating a plurality of micro-channels of uniform shape and dimensions.

According to some embodiments, the pharmaceutical composition is hydrophilic. According to additional embodiments, the pharmaceutical composition comprises at least one hydrophilic therapeutically active agent. According to additional embodiments, the hydrophilic therapeutically active agent within the pharmaceutical composition is selected from the group consisting of proteins, polypeptides, peptides, polynucleotides, oligonucleotides, growth factors, hormones, and salts thereof. According to further embodiments, the polypeptide within the pharmaceutical composition has up to two hundred amino acid residues. In a currently exemplary embodiment, the polypeptide is human growth hormone (hGH). In another currently exemplary embodiment, the polypeptide is human insulin. In further exemplary embodiment, the polypeptide is calcitonin. In a certain exemplary embodiment, the polypeptide is salmon calcitonin. In yet further exemplary embodiment, the polypeptide is parathyroid hormone (PTH) or a fragment thereof. In another exemplary embodiment, the polypeptide is human PTH (hPTH) or a fragment thereof. In a further exemplary embodiment, the polypeptide is an active fragment of hPTH designated hPTH (1-34) having the amino acid sequence from amino acid 1 to amino acid 34 of the full-length hPTH.

According to additional embodiments, the pharmaceutical composition can comprise a preservative, an anti-oxidant, a buffering agent, a stabilizer, and other additives as are well known in the art. According to further embodiments, the stabilizer is a simple or complex carbohydrate. According to certain embodiments, the carbohydrate is selected from the group consisting of mannose, glucose, galactose, raffinose, cellobiose, gentobiose, sucrose and trehalose.

According to some embodiments, the pharmaceutical composition further comprises an acidic component to yield a pH in the range from about 3 to about 6 in solution before drying. In an exemplary embodiment, the pharmaceutical composition comprises hPTH (1-34), sucrose and acetic acid to yield a pH of about 4.0 in solution before drying. In another exemplary embodiment, the pharmaceutical composition comprises hPTH (1-34), trehalose and citric acid to yield a pH of about 4.0 in solution before drying.

According to a further aspect, the present invention provides a printed patch comprising a dried or lyophilized pharmaceutical composition comprising at least one therapeutically active agent. According to one embodiment, the pharmaceutical composition of the printed patch is hydrophilic. According to another embodiment, the therapeutically active agent within the pharmaceutical composition of the printed patch is hydrophilic. According to further embodiments, the therapeutically active agent within the pharmaceutical composition of the printed patch is selected from the group consisting of proteins, polypeptides, peptides, polynucleotides, oligonucleotides, growth factors, hormones, and salts thereof. According to additional embodiments, the polypeptide within the pharmaceutical composition of the printed patch has up to two hundred amino acid residues.

In one currently exemplary embodiment, the pharmaceutical composition within the printed patch comprises human Growth Hormone (hGH), optionally further comprising mannitol and sucrose or trehalose. In another currently exemplary embodiment, the pharmaceutical composition within the printed patch comprises human insulin. In a further embodiment, the pharmaceutical composition within the printed patch comprises a calcitonin. In a certain exemplary embodiment, the pharmaceutical composition within the printed patch comprises salmon calcitonin. In yet further exemplary embodiment, the pharmaceutical composition within the printed patch comprises PTH or a fragment thereof. In a certain exemplary embodiment, the pharmaceutical composition within the printed patch comprises human PTH or a fragment thereof. In another exemplary embodiment, the pharmaceutical composition within the printed patch comprises hPTH (1-34).

The pharmaceutical composition of the printed patch may further comprise a stabilizer. According to some embodiments, the stabilizer can be a simple or complex carbohydrate. According to additional embodiments, the carbohydrate is selected from the group consisting of glucose, galactose, raffinose, cellobiose, gentiobiose, sucrose and trehalose.

The pharmaceutical composition of the printed patch can further comprise an acidic component to yield a pH in the range from 3 to about 6 in solution before drying. According to an exemplary embodiment, the pharmaceutical composition of the printed patch comprises hPTH (1-34), sucrose and acetic acid to yield a pH of about 4.0 in solution before drying. According to additional embodiment, the pharmaceutical composition of the printed patch comprises hPTH (1-34), trehalose and citric acid to yield a pH of about 4.0 in solution before drying.

The printed patch may further comprise an additional hydrophilic dried agent. The patch may also comprise any suitable composition and be of any suitable geometry provided that it is adapted for stable and, optionally microbiologically controlled, aseptic or sterile, storage of the active agent prior to its use.

According to yet another embodiment, the printed patch further comprises at least one of the following: a backing layer, an adhesive layer, and a microporous liner layer.

According to further aspect, the present invention provides a method for preparing a printed patch containing a therapeutically active agent comprising:
  a. preparing a pharmaceutical solution or suspension comprising at least one therapeutically active agent;
  b. placing at least one measured volume of the solution of (a) on a suitable matrix; and
  c. drying the matrix of (b) by drying means that maintain the therapeutic activity of the therapeutically active agent of (a).

The simplicity of the essential ingredients of the patch stems from the fact that the patch is specifically designed for use in conjunction with the apparatus for generating micro-channels in the skin of the subject.

According to additional aspect, the present invention provides a method for transdermal administration of a dried or lyophilized pharmaceutical composition comprising at least one therapeutically active agent using an apparatus and a patch according to the embodiments of the present invention.

The present invention thus provides a method for transdermal administration of a dried or lyophilized pharmaceutical composition comprising: generating a plurality of micro-channels in an area of the skin of a subject; and affixing a patch, preferably a printed patch, comprising a dried or lyophilized pharmaceutical composition comprising at least one therapeutically active agent to the area of skin in which the plurality of micro-channels are present.

According to preferred embodiments the therapeutically active agent in the context of the dried or lyophilized pharmaceutical composition of the invention to be administered according to the method of the present invention is hydrophilic and selected from the group consisting of proteins, polypeptides, peptides, polynucleotides, oligonucleotides and pharmaceutically acceptable salts thereof. Currently exemplary embodiments are human Growth Hormone (hGH), human insulin, calcitonin and PTH. In certain exemplary embodiments, the therapeutically active agent to be administered by the method of the present invention is salmon calcitonin, hPTH, and hPTH (1-34).

According to yet further aspect, the present invention provides a method for transdermal administration of a dried pharmaceutical composition comprising at least one therapeutically active agent, the method comprising: generating a plurality of micro-channels in an area of the skin of a subject;

affixing a patch, preferably a printed patch, comprising a dried pharmaceutical composition comprising a therapeutically effective amount of at least one therapeutically active agent to the area of skin in which the plurality of micro-channels are present; and achieving dose efficiency of at least 10%, thereby attaining a therapeutic effect. According to some embodiments, the therapeutically active agent is a peptide or polypeptide having up to two hundred amino acid residues. Currently exemplary embodiments of peptides or polypeptides are human Growth Hormone (hGH) and human insulin. Currently additional exemplary embodiments are calcitonin and PTH including, but not limited to, salmon calcitonin, human PTH (hPTH) and fragments thereof such as hPTH (1-34). According to one embodiment, the subject is human.

The term "dose efficiency" used herein refers to a calculated ratio (%) between a first calculated amount of a therapeutically active agent present in blood of a subject after transdermal delivery from a patch comprising the active agent, the patch affixed to the skin of the subject where micro-channels have been generated using the apparatus of the present invention, and a second amount of said active agent applied or printed on the patch. The calculated amount of a therapeutically active agent present in the blood of a subject is calculated based on the area under curve (AUC) values over a period of time obtained for the patch compared to the AUC values obtained over the same period of time using a commercially available injectable form of the same active agent.

According to some embodiments, the dose efficiency to be achieved by the method of the invention is of at least 20%. According to additional embodiments, the dose efficiency to be achieved is of at least 30%. According to further embodiments, the dose efficiency is of at least 40%. According to yet further embodiments, the dose efficiency to be achieved is of at least 50%.

According to a still further aspect, the present invention provides a method for treating a bone or cartilage disease or disorder in a subject comprising the steps of:

(a) generating a plurality of micro-channels in an area of the skin of a subject;

(b) affixing a patch to the area of the skin of the subject where the plurality of micro-channels are present, the patch comprising a dried pharmaceutical composition comprising a therapeutically effective amount of a calcitonin, thereby treating the bone or cartilage disease or disorder.

According to some embodiments, the patch is a printed patch according to the principles of the present invention. According to additional embodiments, the pharmaceutical composition further comprises at least one of the constituents selected from the group consisting of a buffering agent, a stabilizer, a preservative, an anti-oxidant, and other additives as known in the art.

According to some embodiments, the clacitonin is selected from the group consisting of salmon calcitonin, eel calcitonin, human calcitonin, rat calcitonin, sheep calcitonin, chicken calcitonin, ox calcitonin, and pig calcitonin. According to additional embodiments, the salmon calcitonin is selected from the group consisting of salmon calcitonin I as set forth in SEQ ID NO: 1, salmon calcitonin II as set forth in SEQ ID NO:2, salmon calcitonin III as set forth in SEQ ID NO:3, salmon calcitonin IV as set forth in SEQ ID NO:4, and salmon calcitonin V as set forth in SEQ ID NO:5. According to a certain embodiment, the salmon calcitonin is salmon calcitonin I.

According to additional embodiments, the bone disease or disorder is selected from the group consisting of osteopenia and osteoporosis in men and women; hypercalcemia; Paget's disease; bone fracture, both vertebral and non-vertebral or bone deficiency; Sudeck's disease; primary or secondary hyperparathyroidism; periodontal disease or defect; metastatic bone disorder; osteolytic bone disease; post-plastic bone surgery; and post-dental implantation. According to a certain embodiment, the bone disease to be treated is osteoporosis in post-menopausal women.

According to further embodiments, the cartilage disease or disorder is selected from the group consisting of osteoarthritis; rheumatoid arthritis; septic arthritis; post-prosthetic joint surgery; and degenerative cartilage loss following traumatic joint injury. According to a certain embodiment, the cartilage disease to be treated is osteoarthritis.

According to further embodiments, generating the plurality of micro-channels in the area of the skin of the subject is at a density of about 75 to about 450 micro-channels/cm$^2$. According to certain embodiments, generating the plurality of micro-channels in the area of the skin of the subject is at a density of about 150 to about 300 micro-channels/cm$^2$. Preferably, the plurality of micro-channels has uniform shape and dimensions.

It is to be understood that the method of the present invention, which comprises generating a plurality of micro-channels is preferably performed by the apparatus of the present invention, which apparatus comprises an electrode cartridge comprising a plurality of electrodes and a main unit comprising a control unit, which is adapted to apply electric energy between the plurality of electrodes. According to some embodiments, the electrodes have a diameter of about 30 microns to about 150 microns. According to certain embodiments, the electrodes have a diameter of about 80 microns. According to further embodiments, the electrodes have a length of about 50 microns to about 100 microns. According to certain embodiments, the electrodes have a length of about 95 microns. According to additional embodiments, the electrical energy applied by the control unit of the apparatus of the present invention is of radio frequency.

According to certain embodiments, the present invention incorporates the techniques for creating micro-channels by inducing ablation of the stratum corneum using radio frequency (RF) energy, including the apparatus referred to as ViaDerm or MicroDerm, disclosed in one or more of the following: U.S. Pat. No. 6,148,232; U.S. Pat. No. 6,597,946; U.S. Pat. No. 6,611,706; U.S. Pat. No. 6,711,435; U.S. Pat. No. 6,708,060; Sintov et al., J. Controlled Release 89: 311-320, 2003; the content of which is incorporated by reference as if fully set forth herein. It is however emphasized that although some preferred embodiments of the present invention relate to transdermal delivery obtained by ablating the skin by the aforementioned apparatus, substantially any method known in the art for generating channels in the skin of a subject may be used.

BRIEF DESCRIPTION OF THE DRAWINGS

The present invention will be more fully understood from the following detailed description of the preferred embodiments thereof as illustrated by the appended figures, wherein.

DETAILED DESCRIPTION OF THE INVENTION

Figure 1:
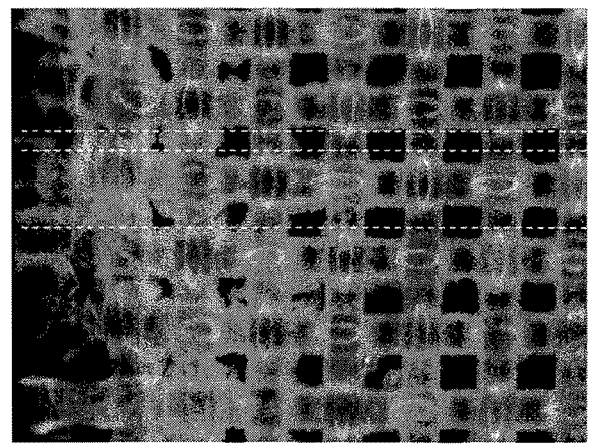
FIG. 1 is a view of a printed patch consisting of rhGH dried solution and a polyester screen.

The present invention provides formulations, methods and pharmaceutical technologies for delivering dried or lyophilized medications, preferably of hygroscopic formulations, through treated skin in which micro-channels have been generated.

The current transdermal patches are designed to deliver drug molecules through the stratum corneum (SC). As such they have several characteristics:
 a. The delivery of the molecules occurs through all the area under the patch.
 b. The interface between the patch and the skin tends to be hydrophobic. This facilitates delivery of drug molecules from one hydrophobic matrix (patch) to the other (SC).
 c. The patches usually contain enhancers. The purpose of these molecules is to change and disrupt the structure of the SC, thus elevating the solubility of the drug molecules in the SC matrix. Enhancers are also responsible for undesired side effects like erythema, edema or pruritis.

Micro-channel or electroporation treatment creates aqueous micro-channels through the into the epidermis, thus drug molecules do not need to pass through the lipoid SC in order to get into viable tissues. This has several implications:
 1. The delivery of the molecules occurs mainly through the micro-channels, which occupy less than 1% of the treated skin area.
 2. The transdermal delivery rate of agents through the micro-channels is not restricted by the limited permeability of the SC.
 3. There is no need to include enhancers in the formulations, thus improving skin safety.

Based on these considerations, the system of the present invention is highly suitable for delivery of dried or lyophilized hydrophilic macromolecules through the new skin environment, which is created by the ablation of the stratum corneum. The main advantage of using dried or lyophilized formulations is the potential stability of the pharmaceutically active ingredients as compared with liquid formulations. This advantage is especially relevant for active ingredients in the form of peptides and proteins. Accordingly, a variety of formulations may provide efficient delivery of a variety of drugs, particularly and advantageously of dried or lyophilized hygroscopic formulations. As a consequence, the system of the present invention does not necessitate the use of permeation enhancers for transdermal drug delivery and is therefore not susceptible to the problems attendant therewith, particularly irritation. Irritation occurs as the skin reacts to topically applied agents, particularly those maintained under occlusion, by blistering or reddening accompanied by unpleasant burning, itching, and stinging sensations. It is desirable to avoid or to keep the number of possibly irritating agents in a transdermal delivery system to a minimum.

It is now disclosed for the first time that use of a patch comprising a dried or lyophilized pharmaceutical composition comprising a therapeutically active agent, placed on an area of the skin pretreated by an apparatus that generates micro-channels provides unexpectedly therapeutically effective serum levels of the active agent. The dose efficiency or bioavailability obtained was adequate to provide therapeutic effects in a subject. Moreover, these unexpected results were achieved even for very large molecules with low diffusion coefficient.

These results were totally unexpected due to the fact that usually in transdermal delivery, bioavailability values low. For example, estradiol patch (Climara® by 3M) or testosterone patch (Androderm® (by TheraTech, Inc.) are known to achieve bioavailability values of about 9% or 20%, respectively.

The term "dried or lyophilized pharmaceutical composition" as used in the context of the present specification and claims refers to a pharmaceutical composition of which the residual moisture is below 20%, preferably below 10%, more preferably below 5%, and most preferably below 3% of the final composition's weight.

The term "micro-channel" as used in the context of the present specification and claims refers to a hydrophilic pathway generally extending from the surface of the skin through all or a significant part of the stratum corneum and may reach into the epidermis or dermis, through which molecules can diffuse. Although some preferred embodiments of the present invention are described with respect to ablating the stratum corneum by electric current or spark generation, preferably at radio frequency (RF), substantially any method known in the art for generating channels in the skin of a subject may be used (see e.g. U.S. Pat. Nos. 5,885,211, 6,022,316, 6,142,939, 6,173,202, 6,148,232 and WO 02/085451 and WO 02/092163). The term "micro-pore" is used interchangeably herein.

The term "new skin environment" as used herein, denotes a skin region created by the ablation of the stratum corneum and formation of at least one micro-channel, using the system of the present invention.

Suitable therapeutically active agents for use in conjunction with the principles of the invention are dried or lyophilized large molecules, including a wide variety of proteins, polypeptides, peptides, polynucleotides, oligonucleotides, other bioactive molecules and pharmaceutically acceptable salts thereof including, but not limited to, insulin, proinsulin, follicle stimulating hormone, insulin like growth factor-1 and insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, clotting factors such as factor VIIIC, factor IX, tissue factor, and von Willebrand factor, anti-clotting factors such as Protein C, atrial natriuretic factor, lung surfactant, plasminogen activator, such as urokinase or tissue-type plasminogen activator, including human tissue-type plasminogen activator (t-PA), bombesin, thrombin, enkephalinase, collagen; a collagen domain, mullerian-inhibiting agent, relaxin A-chain, relaxin B-chain, prorelaxin, Dnase, inhibin, activin, vascular endothelial growth factor, receptors for hormones or growth factors, integrin, protein A or D, rheumatoid factors, neurotrophic factor such as bone-derived neurotrophic factor (BDNF), neurotrophin-3, -4, -5, and -6 (NT-3, NT-4, NT-5, or NT-6), CD proteins such as CD-3, CD-4, CD-8, and CD-19, osteoinductive factors, immunotoxins, interferon such as interferon-alpha, -beta, and -gamma, colony stimulating factors (CSFs), e.g., M-CSF, GM-CSF, and G-CSF, interleukins (ILs), e.g., IL-1 to IL-10, superoxide dismutase, T-cell receptors, surface membrane proteins, decay accelerating factor, viral antigen such as, for example, a portion of the AIDS envelope, transport proteins, homing receptors, addressins, regulatory proteins, antibodies, analogs and fragments of any of the above-listed polypeptides. According to some preferred embodiments, the therapeutically active agent is a peptide or polypeptide having up to two hundred amino acid residues. Examples of peptides or polypeptides include, but not limited to, human growth hormone, human insulin, human parathyroid hormone (hPTH), and fragments thereof. Examples of hPTH fragments include, but are not limited to, hPTH (1-34), hPTH (1-37), hPTH (1-38), and hPTH (1-41). Examples of calcitonins include, but are not limited to, salmon calcitonin, eel calcitonin, human calcitonin, rat calcitonin, chicken calcitonin, ox calcitonin, pig calcitonin, and sheep calcitonin. According to some embodiments, salmon calcitonin is selected from the group consisting of salmon calcitonin I of the amino acid sequence:
CSNLSTCVLGKLSQELHKLQTYPRTNTGSGTP as set forth in SEQ ID NO:1; salmon calcitonin II of the amino acid sequence:
CSNLSTCVLGKLSQDLHKLQTFPRTNTGAGVP as set forth in SEQ ID NO:2; salmon calcitonin III of the amino acid sequence:
CSNLSTCMLGKLSQDLHKLQTFPRTNTGAGVP as set forth in SEQ ID NO:3; salmon calcitonin IV of the amino acid sequence:
CSNLSTCVLGKLSQDLHKLQTFPRTDVGAGTP as set forth in SEQ ID NO:4; and salmon calcitonin V of the amino acid sequence:
CSNLSTCMLGKLSQDLHKLQTFPRTDVGAGTP as set forth in SEQ ID NO:5.

According to a certain embodiment, the calcitonin is salmon calcitonin I.

As used herein, "a pharmaceutically acceptable salt" refers to a derivative of the disclosed agents wherein the parent agent is modified by making acid or base salts of the agent. For example, acid salts are prepared from the free base (typically wherein the neutral form of the drug has a neutral —$NH_2$ group) using conventional means known in the art, involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. Conversely, preparation of basic salts of acid moieties which may be present on a drug are prepared using a pharmaceutically acceptable base such as sodium hydroxide, potassium hydroxide, ammonium hydroxide, calcium hydroxide, trimethylamine, or the like.

Several general embodiments are covered by the invention, including embodiments in which the therapeutically active agent in the dried pharmaceutical composition is hydrophilic and embodiments in which the dried pharmaceutical composition further comprises an inert (not containing a drug) hydrophilic dried agent. It is known in the art that a combination of dried hGH with mannitol may be advantageous for dissolution of the hGH powder.

As used herein, "pharmaceutical composition" or "medication" used herein interchangeably, refers to a pharmaceutical composition comprising a therapeutically effective amount of an active agent, wherein the pharmaceutical composition or medication may be dried or lyophilized while retaining a therapeutic activity. The terms "therapeutically active agent" and "drug" are used herein interchangeably to denote the active ingredient of the pharmaceutical composition.

In a preferred embodiment of the present invention, the dried pharmaceutical composition can comprise more than one therapeutically active agent.

The pharmaceutical composition for use according to principle of the invention can be optimized to take into consideration issues like stability. In this specification the term "stable" refers to a composition that is robust enough to retain at least 80% of the active ingredient in its original chemical form for a period of at least three months at ambient or below ambient temperatures.

According to the invention, the dried or lyophilized pharmaceutical composition may comprise at least one stabilizer. "Stabilizers" as defined herein stabilize an active agent, preferably a protein, a polypeptide, or a peptide, during storage. Stabilizers may also aid delivery of the active agent. Stabilizers known in the art include, but are not limited to, carbohydrates such as, for example, mannose, glucose, galactose, raffinose, cellobiose, gentiobiose, sucrose and trehalose, and hydrophobically-derivatised carbohydrates (HDCS) such as sorbitol hexaacetate, α-glucose pentaacetate, β-glucose pentaacetate, trehalose octaacetate, trehalose octapropanoate, sucrose octaacetate, sucrose octapropanoate, cellobiose octaacetate, cellobiose octapropanoate, raffinose undecaacetate and raffinose undecapropanoate. The composition may also comprise an amino acid so as to increase drug stability. Amino acids that may be added to the pharmaceutical composition include, but are not limited to, histidine and glutamic acid.

Typically, proteins modified by a covalent attachment of water-soluble polymers are known to exhibit substantially longer half-lives in blood following intravenous injection than do the corresponding unmodified proteins. Such modifications may also increase the protein's solubility in aqueous solution, eliminate aggregation, enhance the physical and chemical stability of the protein, and greatly reduce the immunogenicity and antigenicity of the protein. Thus, the pharmaceutical composition according to the present invention may comprise polymers, preferably water-soluble polymers such as polyethylene glycol, copolymers of polyethylene glycol and polypropylene glycol, carboxymethyl cellulose, dextran, polyvinyl alcohol, polyvinylpyrrolidone or polyproline, hydroxypropyl metharylamide, and the like.

The pharmaceutical composition may also include diluents of various buffer content (e.g., Tris-HCl, phosphate, citrate, acetate), pH and ionic strength, additives such as albumin or gelatin to prevent adsorption to surfaces, detergents (e.g., Tween 20, Tween 80, Pluronic F68, Pluronic 127), anti-oxidants (e.g., ascorbic acid, sodium metabisulfite), and preservatives (e.g., Thimerosal, benzyl alcohol, parabens, m-cresol). The formulation of the pharmaceutical composition comprising a therapeutically active agent according to the present invention is determined so as to provide improved stability of the active agent while retaining or improving its bioavailability. Methods to detect stability of an agent are exemplified herein below by HPLC analysis. However, other methods known in the art may be used to determine the stability of an active agent.

The amount of therapeutically active agent in the pharmaceutical composition necessary to provide the desired amounts and concentration in the serum can be determined by methods described herein below and by methods known in the art. Thus, the concentration or the quantity of the therapeutically active agent per dried pharmaceutically composition or per patch can be varied independently in order to achieve a desired therapeutic effect.

Powder Patch

The present invention discloses for the first time the use of patches that comprise a dry pharmaceutical composition, as a delivery system for hydrophilic macromolecules, such as peptides or proteins, as well as for other highly water soluble drugs. After application of such a patch on the pretreated new skin environment, the pharmaceutical composition is dissolved in fluid that comes out of the micro-channels, and is then absorbed through the micro-channels into the body. This approach is particularly suitable for drugs that do not irritate the skin even at high concentrations.

According to certain embodiments of the present invention, it is possible to monitor and to obtain a relative evaluation of the loss of fluids that come out from the micro-channels in the new skin environment with respect to the loss of fluids that come out from the skin prior to ablation of the stratum corneum. This type of measurement is also termed herein "transepidermal water loss" or "TEWL", and is described in the foregoing examples.

Thus, a patch based on a drug in the solid state may have several advantages:
 i. Improved stability, due to the absence of solvents and other excipients;
 ii. Relatively high delivery rates, due to the delivery from a saturated solution or suspension;
 iii. May enable production of thin and convenient patch, instead of reservoir patches, even for sensitive active materials that are not suitable for a drug-containing adhesive type of patch;
 iv. Practical as it enables usage of very small amounts of expensive agents.

Methods for preparing different types of powder patches, specifically methods that are suitable for accurately placing small amounts of an active agent including proteins, as a dry agent onto a solid support from which they will be released are disclosed herein.

A. Printing

Printing methods encompass techniques in which small droplets of a solution or suspension of a pharmaceutical composition are placed on a uniform liner in a controlled manner. The droplets dry rapidly and leave solid dots of the pharmaceutical composition. The dose is accurately determined by the concentration of the active agent in the solution or suspension and the configuration and programming of the manufacturing instrument. Besides the therapeutically active agent, the pharmaceutical composition may advantageously include other materials, such as solubility increasing agents, stabilizers, and polymers.

In order to penetrate into the skin and the blood circulation, the pharmaceutical composition within the printed dots on the liner is dissolved in the fluids that are exuded from the skin through micro-channels.

Methods known in the art for applying droplets include a small volume (one to several microliter) syringe or an array of syringes, a combination of a small volume syringe or an array of syringes with a metering pump, an array of small pins, tips of the pins dipped in the solution/suspension, printing with a device like an ink jet printer, printing with a cartridge containing the solution of the pharmaceutical composition, spraying of a thin film of a solution of active drug on a liner and the like.

To enable adhesion of the printed patch to the new environment skin the printing is prepared on a transdermal adhesive backing liner. Alternatively, a suitable adhesive can be printed between the prints of the drug, on a non-adherent liner.

B. Non-Uniform Liners

Suitable liners for this purpose are various liners with precise cavities. Basically the liner is dipped or soaked in the solution of the therapeutically active material, and then dried by air-drying or lyophilization or any other suitable means of drying or evaporation. The amount of solution of therapeutically active material that is applied on the liner is determined by the structure of the liner itself and its chemical and surface characteristics.

Various methods for preparing non-uniform dried drug-containing liners are known in the art including soaking a filter paper or a filter membrane with the solution of the drug and drying it, dipping a micronic net or screen into the active solution and drying it (as exemplified herein below), using a sheet with small and precise indentations or pores in a specific density or pattern and either filling the pores with the solution of the active drug, and drying or flipping the indentation so as to leave the active powder film on the protruding convexities, preparing a sheet with small projections on it then dipping the tips of the projections into the pharmaceutical active solution such that a small drop is left on each projection and drying.

Drying can be carried under controlled conditions for example by changing the temperature, humidity or pressure.

Various types of materials may be used to form the liners, including without limitation screens and fabrics in various pattern and synthetic woven meshes prepared from various polymers selected from the group of polyamide, polyester, polypropylene, Teflon, poly olefins such as polyethylene and polybutylene, polyurethane, polyvinyl butyrate, polysulphone, polyethersulphone, polyvinyl chloride, polycarbonate, polytetrafluoroethylene, polyvinylidene fluoride, cellulose acetate, cellulose triacetate, cellulose nitrate. A current preferred liner material is a polyester screen containing a mesh of 45 µm and 39% open area. Another preferred material is a dense nylon (polyamide) fabric (as exemplified herein below by Sefar Nitex™, G Bopp & Co Ltd, Derbyshire, UK).

C. Direct Application of Powder

A basic approach for the application of pharmaceutical powder is to directly apply the powder on the treatment site. According to one embodiment, spots of powder are embedded onto a soft flat sheet that is attached to the new skin environment by an additional adhesive layer. Alternatively, the sheet itself may be self-adherent. According to a second embodiment the powder is encapsulated within water-soluble films. The powder capsules can be prepared by distributing the powder over a water-soluble film containing an array of wells, filling the wells and removing excessive powder. The sheet is then covered with a similar sheet, such that the wells of both sheets are at similar positions. Alternatively, the pores in the water-soluble sheet are covered with a flat sheet, which is a water-soluble film. The powder patch can be then attached to the skin such that either the flat sheet or the well-containing sheet is facing the new skin environment. The flat sheet may be also made of a non-soluble backing liner.

To enable adhesion to the new skin environment the drug powder can be dispersed over a liner, which contains microscopic suction cups on its surface.

The powder patch according to the present invention may be further incorporated into a medical patch. The medical patch comprising the powder patch may further comprise at least one of the following: a backing layer, an adhesive, and a suitable microporous liner layer such that the drug containing layer is disposed between the backing layer and the microporous liner layer.

The term "backing layer" defines any protective layer not permeable to the drug that is provided to physically seal and hence protect the patch, specifically the drug containing layer. The backing layer may be made of a polyester, polyethylene or polypropylene.

Application of a medical patch to the new skin environment is accomplished after at least partial removal of any covering or packaging, before use. This exposes the drug-containing layer, which may itself have adhesive properties, or may further comprise an adhesive layer attached to the drug-containing layer. Proper adherence to usage instructions generally ensures that the patch can be placed in a sterile manner.

According to the invention the powder patch may be modular so as to contain in each module a known amount of the therapeutically active agent. A known amount of the active agent may be, for example, a unit dose. Thus, affixing the modular patch to the new skin environment will enable transdermal delivery of an accurate and controlled dosage of the therapeutically active agent.

Devices for Enhancing Transdermal Delivery of Dried or Lyophilized Medication

The system of the present invention further contains an apparatus for enhancing transdermal delivery of an agent. According to the principles of the invention the apparatus is used to generate a new skin environment through which a dried or lyophilized medication is delivered efficiently.

In preferred embodiment of the present invention, the apparatus for enhancing transdermal delivery of an agent using RF energy is as disclosed in U.S. Pat. No. 6,148,232 and continuations thereto (U.S. Pat. Nos. 6,597,946; 6,611,706; 6,711,435; 6,708,060; and Sintov et al. J. Controlled Release 89: 311-320, 2003, the content of which is incorporated by reference as if fully set forth), comprising: an electrode cartridge, optionally removable, comprising at least one electrode and a main unit wherein the main unit loaded with the electrode cartridge is also denoted herein ViaDerm.

The control unit is adapted to apply electrical energy to the electrode typically by generating current flow or one or more sparks when the electrode cartridge is in vicinity of the skin. The electrical energy in each electrode within the electrode array causes ablation of stratum corneum in an area beneath the electrode, thereby generating at least one micro-channel.

The control unit comprises circuitry which enables to control the magnitude, frequency, and/or duration of the electrical energy delivered to an electrode, in order to control current flow or spark generation, and consequently to control the dimensions and shape of the resulting micro-channel. Typically, the electrode cartridge is discarded after one use, and as such is designed for easy attachment to the main unit and subsequent detachment from the unit.

To minimize the chance of contamination of the cartridge and its associated electrodes, attachment and detachment of the cartridge is performed without the user physically touching the cartridge. Preferably, cartridges are sealed in a sterile cartridge holder, which is opened immediately prior to use, whereupon the main unit is brought in contact with a top surface of the cartridge, so as to engage a mechanism that locks the cartridge to the main unit. A simple means of unlocking and ejecting the cartridge, which does not require the user to touch the cartridge, is also provided.

Optionally the electrode cartridge may further comprise means to mark the region of the skin where micro-channels have been created, such that a medical patch can be precisely placed over the treated region of the skin. It is noted that micro-channel generation (when practiced in accordance with the techniques described in the above-cited US patent or continuation patent applications to Avrahami et al., assigned to the assignee of the present patent application) does not generally leave any visible mark, because even the large number of micro-channels typically generated are not associated with appreciable irritation to the new skin environment.

The term "about" used herein refers generally to variation within one standard deviation of the mean.

Methods for Using the System of the Invention

The current invention also provides a method for treatment with a dried or lyophilized medication using the system of the invention. In general embodiments, the procedure for forming the new skin environment comprises the step of placing over the skin the apparatus for generating at least one micro-channel. Preferably, prior to generating the micro-channels the treatment sites will be swabbed with sterile alcohol pads. Preferably, the site should be allowed to dry before treatment.

In preferred embodiments of the current invention, the type of apparatus used to generate micro-channels is disclosed in U.S. Pat. No. 6,148,232 and Sintov et al. J. Controlled Release 89: 311-320, 2003. The apparatus, containing the electrode array, is placed over the site of treatment, the array is energized by RF energy, and treatment is initiated. In principle, the ablation and generation of micro-channels is completed within seconds. The apparatus is removed after micro-channels are generated at limited depth, preferably limited to the depth of the SC and the epidermis. Any patch known in the art that is suitable for usage in the system of the invention as described above, comprising a therapeutically active agent, is attached to the new skin environment.

The present invention further provides a method for transdermal administration of a dried pharmaceutical composition comprising therapeutically active agent, the method comprising: generating a plurality of micro-channels in a region of the skin of a subject, affixing a patch comprising a dried pharmaceutical composition comprising a therapeutically effective amount of a therapeutically active agent to the region of skin in which the micro-channels are present, and achieving dose efficiency of at least 10%, thereby attaining a therapeutically effective blood concentration of the active agent for at least a therapeutically relevant period of time leading to a therapeutic effect.

As defined herein "therapeutically effective blood concentration" means a concentration of an active agent, which results in a therapeutic effect, preferably in humans. Blood concentrations at ranges expected to exert therapeutic effect are obtained in animal models. As exemplified herein below therapeutic blood concentrations of human insulin in hyperglycemic rats, which result in normal glucose level (100 mg/dl to 200 mg/dl glucose) were obtained within approximately 1-3 hours for a period of about 4-6 hours. It is to be understood that the present invention encompasses methods for transdermal administration of a dried pharmaceutical composition, which achieve therapeutic blood concentrations for longer periods of time. Additionally, as therapeutic blood concentrations of hydrophilic active agents of the invention are known in the art, the period of time for achieving and maintaining therapeutic blood concentrations can be determined by methods described herein below or by any other method known in the art. For example, therapeutic blood concentrations of hPTH (1-34) in human ranges from about 20 to 250 pg/ml for a period of 2-4 hours.

The present invention encompasses methods for transdermal administration of a dried pharmaceutical composition comprising a therapeutically active agent, wherein the active agent is a peptide or polypeptide having up to two hundred amino acid residues. Examples of peptides or polypeptides, which can be administered transdermally by the methods of the present invention include, but are not limited to, hGH, human insulin, calcitonin, human PTH or a fragment thereof. Human PTH fragments that can be administered transdermally by the methods of the present invention include, but are not limited to, hPTH (1-34), hPTH (1-37), hPTH (1-38), hPTH (1-41), and hPTH (1-84).

The term "dose efficiency" used herein refers to a calculated ratio (%) between a first estimated amount of a therapeutically active agent present in blood of a subject after transdermal delivery from a patch comprising the active agent, the patch affixed to the skin of the subject where micro-channels have been generated using the apparatus of the present invention, and a second amount of said active agent applied or printed on the patch.

In pharmacokinetic studies, relative bioavailability reflects the bioavailability of a drug administered by any route of administration, other than I.V. injection, to the bioavailability of the same drug injected at the same dose I.V. If the drug is administered transdermally, relative bioavailability is calculated according to formula I:

$$(AUC_{transdermal}/Dose_{transdermal})/(AUC_{IV}/Dose_{IV})*100 = \text{Relative Bioavailability (\%)}.$$

In formula I, AUC defines the area under curve when measuring drug concentration in blood along a predetermined period of time, the dose of the drug administered transdermally is identical to the dose of the drug administered intravenously.

However, due to the fact that it is not clinically feasible to inject to a human subject the same dose of a drug or active agent as applied on a patch, the inventors of the present invention calculated dose efficiency, which provides an estimate of the relative bioavailability. Dose efficiency is calculated according to formula II:

$$(AUC_{transdermal}/Dose_{transdermal})/(AUC_{SC}/Dose_{SC})*100 = \text{Dose efficiency (\%)}.$$

In formula II, the dose of the drug or active agent administered transdermally is generally higher than the dose of the drug or active agent administered subcutaneously and the administration route, which is used as a reference, is subcutaneous administration rather than I.V. injection. AUC defines the area under curve when measuring drug or active agent concentration in blood along a predetermined period of time. Thus, for calculating dose efficiency of a therapeutically active agent such as, for example, hPTH (1-34), administered transdermally from a patch to human subjects, a dose of 20 µg of hPTH (1-34) was injected subcutaneously, which dose is approved by the FDA, and the $AUC_{SC}$ of 20 µg of hPTH (1-34) along 12 hrs was used as 100%. A higher dose of hPTH (1-34) was applied or printed on a patch and the $AUC_{transdermal}$ of hPTH (1-34) was measured along the same period of time, i.e., 12 hrs. The $AUC_{SC}$ of 20 µg of hPTH (1-34), taken as 100%, was then used to calculate the amount of hPTH (1-34) delivered transdermally from the patch, based on the $AUC_{transdermal}$ measured. The calculated amount of hPTH (1-34) delivered transdermally was then divided by the amount of hPTH (1-34) applied or printed originally on the patch, and that ratio was used as a measure of dose efficiency. It is to be understood that the term "bioavailability" as used herein is proportional to the term "dose efficiency", the two terms are used interchangeably throughout the specification and claims.

The present invention further provides a method for preventing or treating a bone or cartilage disease or disorder in a subject comprising the steps of: (a) generating a plurality of micro-channels in an area of the skin of the subject in need of such treatment; and (b) affixing a patch to the area of the skin where the plurality of micro-channels are present, the patch comprises a dried or lyophilized pharmaceutical composition comprising a therapeutically effective amount of a calcitonin, thereby preventing or treating the bone or cartilage disease or disorder. It is to be understood that the present invention encompasses any disease or condition for which calcitonin would have a beneficial pharmacological effect.

The term "treating" as used herein include preventative (e.g., prophylactic), palliative and curative treatment. Thus, the method of the present invention is useful for improving tissue function in a subject having, or at risk of, bone or cartilage disease or disorder. According to one embodiment, the subject is a human.

The term "therapeutically effective amount" as used herein refers to that amount of a calcitonin which provides a therapeutic effect for a given disease or disorder and administration regimen.

The term "calcitonin" as used herein is intended to refer to that class of pharmacologically active polypeptides including not only naturally occurring calcitonins but also various derivatives and analogs thereof, e.g., in which one or more of the amino acid residues or sequences naturally present is omitted, replaced, reversed or otherwise derivatized, or in which the N- or C-terminal is modified. Thus, the general term calcitonin, as used hereinafter, is intended to mean all such calcitonins whether naturally occurring or synthetic.

Examples of naturally occurring calcitonins include salmon calcitonin (CAS RN=47931-85-1); human calcitonin, Chemical Abstract Service Registry Number (CAS RN)=21215-62-3; rat calcitonin (CAS RN=11118-25-5); eel calcitonin (CAS RN=57014-02-5); chicken calcitonin I (CAS RN=96157-98-1); chicken calcitonin II (CAS RN=103468-65-1); ox calcitonin (CAS RN=26112-29-8); pig calcitonin (CAS RN=12321-44-7); and sheep calcitonin (CAS RN=40988-57-6). According to a certain embodiment, the calcitonin is salmon calcitonin.

Salmon calcitonin include salmon calcitonin I, II, III, IV, and V of the amino acid sequences as set forth in SEQ ID NOs: 1 to 5, respectively (see, for example, Breimer et al. Biochem. J. 255: 377-390, 1988; Pless et al., Nature New Biol. 240: 62-63, 1972; Jansz et al., Proc. Natl. Acad. Sci. U.S.A 93: 12344-12348, 1996; Katafuchi et al., J. Biol. Chem. 278: 12046-12054, 2003, the contents of which is incorporated as if fully set forth herein).

Examples of calcitonins wherein one or more amino acids have been omitted are the des-[Ser 2, Tyr 22]-Gly$^8$-calcitonins described in U.S. Pat. No. 4,597,900 and the des-[Tyr 22]-salmon calcitonin described in U.S. Pat. No. 4,304,692.

Examples of calcitonins wherein the naturally occurring sequence has been modified include the 1,7-dicarba-calcitonins such as eel 1,7-dicarbacalcitonin (elcatonin CAS RN=60731-46-6); salmon 1,7-dicarbacalcitonin (CAS RN=60864-37-1); and human 1,7-dicarbacalcitonin (CAS RN=66811-56-1).

The bone diseases or disorders include, without limitation, osteopenia and osteoporosis; bone fracture of both vertebral and non-vertebral; bone deficiency; Paget's disease; primary or secondary hyperparathyroidism; periodontal disease or defect; metastatic bone disorder; osteolytic bone disease; post-plastic bone surgery; post-dental implantation; hypercalcemia; and renal osteodystrophy.

The cartilage diseases or disorders include, without limitation, osteoarthritis; rheumatoid arthritis; septic arthritis; post-prosthetic joint surgery; and degenerative cartilage loss following traumatic joint injury.

According to one embodiment, the subject to be treated by the method of the invention is a human at risk or suffering from osteoporosis. Typically, a human at risk for osteoporosis is a postmenopausal woman, or a premenopausal, hypogonadal woman.

According to another embodiment, the subject to be treated is a human at risk or suffering from osteoarthritis.

Affixing the patch comprising a calcitonin to the human subject's skin can be performed regularly (e.g., once, twice, or more times each day or week), intermittently (e.g., irregularly during a day or week), or cyclically (e.g., regularly for a period of days or weeks followed by a period without administration).

The method for preventing or treating a bone or cartilage disease or disorder can be combined with other therapies known for treating such disorders. For example, calcitonin can be administered with parathyroid hormone (PTH). Calcitonin can be administered with other antiresorptive agents such as estrogen, vitamin D or derivatives or metabolites thereof. Similarly, IGF-1, statins, selective estrogen receptor modulators (SREMs), or any other anabolic or antiresorptive agent known in the art can be administered with calcitonin in a combination therapy. It is to be understood that administering the anabolic or antiresorptive agent can be preformed by any route of administration known in the art, such as intravenously, intraarterially, subcutaneously, intradermally, intraperitoneally, or intramuscularly.

According to preferred embodiments of the current invention, the micro-channels may be generated separately or simultaneously with the application of a medical patch. Among the other applications, the system may include a medical patch comprising an adhesive cut-out template which is placed on the skin, and through which the cartridge is placed to treat the region of skin exposed through the template. The dried or lyophilized medication, contained within a printed patch or any other suitable patch according to embodiments of the present invention, is attached to the template, which is to be placed over the treated region of skin. In these applications, after removing a protective backing, the template portion of the medical patch is placed on the skin and secured by the adhesive. An electrode cartridge is then affixed to the handle, the user holds the handle so as to place the cartridge against the region of skin inside the template, and the electrodes are energized to treat the skin. Subsequently, the cartridge is discarded. A protective covering is then removed from the medicated matrix by pulling on a tab projecting from the covering, so as to concurrently lift and place the medicated matrix over the treated region of skin. It is noted that the integration of the template and the patch into a single unit assists the user in accurately placing the medicated patch onto the treated area of skin. Utilizing the system of the invention in this manner becomes advantageous for disinfected applications.

For still other applications, an integrated electrode/medicated pad cartridge is used, to provide a practical apparatus as disclosed in International Patent Application WO 02/092163 which is assigned to the assignee of the present patent application and incorporated herein by reference and is also denoted MicroDerm. In these applications, the cartridge comprises an electrode array, a controlled unit and a medicated pad. Accordingly, no template is typically required. The user places the electrodes against the skin and this contact is sufficient to initiate current flow or spark formation within the electrode and the subsequent formation of micro-channels. An adhesive strip, coupled to the bottom of the medicated pad, comes in contact with and sticks to the skin when the electrodes are placed against the skin. A top cover on the medicated matrix is coupled to the electrode region of the cartridge, such that as the electrode region, fixed to the handle, is removed from the skin the top cover is pulled off the medicated pad and the pad is concurrently folded over the treated region of skin. This type of application eliminates the need for the user to touch any parts of the electrode cartridge or the medicated pad, thus substantially reducing or eliminating the likelihood of the user contaminating the apparatus.

In a preferred embodiment, current may be applied to the skin in order to ablate the stratum corneum by heating the cells. In one preferred embodiment, spark generation, cessation of spark generation, or a specific current level may be used as a form of feedback, which indicates that the desired depth has been reached and current application should be terminated. For these applications, the electrodes are preferably shaped and/or supported in a cartridge that is conducive to facilitating ablation of the stratum corneum and the epidermis to the desired depth, but not beyond that depth. Alternatively, the current may be configured so as to ablate the stratum corneum without the generation of sparks.

The present invention incorporates methods and apparatus described in International Patent Application WO 02/092163 entitled "Monopolar and bipolar current application for transdermal drug delivery and analyte extraction," which is assigned to the assignee of the present patent application and incorporated herein by reference. For example, this application describes maintaining the ablating electrodes either in contact with the skin or up to a distance of about 500 microns therefrom. The application further describes spark-induced ablation of the stratum corneum by applying a field having a frequency between about 10 kHz and 4000 kHz, preferably between about 10 kHz and 500 kHz.

Alternatively or additionally, preferred embodiments of the present invention incorporate methods and apparatus described in International Patent Application WO 02/085451 entitled "Handheld apparatus and method for transdermal drug delivery and analyte extraction," which is incorporated herein by reference.

Still further alternatively or additionally, preferred embodiments of the present invention incorporate methods and apparatus described in the above-cited U.S. Pat. No. 6,148,232 to Avrahami, which is assigned to the assignee of the present patent application and incorporated herein by reference.

In some preferred embodiments of the present invention, the cartridge supports an array of electrodes, preferably closely spaced electrodes, which act together to produce a high micro-channel density in an area of the skin under the cartridge. Typically, however, the overall area of micro-channels generated in the stratum corneum is small compared to the total area covered by the electrode array.

In further preferred embodiments of the present invention, a concentric electrode set is formed by employing the skin contact surface of the cartridge as a return path for the current passing from the electrode array to the skin. Preferably, the cartridge has a relatively large contact surface area with the skin, resulting in relatively low current densities in the skin near the cartridge, and thus no significant heating or substantial damage to the skin at the contact surface.

In proximity to each electrode in the electrode array, by contrast, the high-energy applied field typically induces very rapid heating and ablation of the stratum corneum.

Having now generally described the invention, the same will be more readily understood through reference to the following examples, which are provided by way of illustration and are not intended to be limiting of the present invention.

EXAMPLES

Human growth hormone (hGH) is a 22 kDa polypeptide hormone that was chosen, in its recombinant form (rhGH) to represent the transdermal delivery capacity of a large, hydrophilic molecules using a printed patch and ViaDerm technology.

GH is produced by the pituitary gland (hypophysis) and acts in several ways and on several targets. A distinctive role attributed to GH is the induction of IGF-1 production by liver cells (hepatocytes). As GH is the main trigger for the production of IGF-1, the activity of GH can be detected by measuring IGF-1 levels in the blood. GH levels in the blood can be directly analyzed as well.

In hypophysectomized animals, IGF-1 levels are expected to be negligible without treatment and dose dependant in treated animals.

The test article chosen for this study is GENOTROPIN® (Pharmacia & Upjohn, Sweden) which contains a recombinant hGH (one dose contains 16 IU, 5.3 mg) synthesized by a modified strain of E. Coli and designed for subcutaneous injection, and mannitol (1.5 mg).

The presence of mannitol, which is a hygroscopic agent, in the rhGH composition of GENOTROPIN®, is important. According to the principle of the present invention the powder patches are applied on a pre-treated skin containing hydrophilic micro-channels such as those formed by ViaDerm. The pharmaceutical powder, which is hygroscopic due to its mannitol content, is dissolved in the exudates from the micro-channels hence enabling an efficient transdermal delivery of the drug.

Example 1

Preparation of rhGH Printed Powder Patch

Essentially, the printed-patches were prepared by spotting precise small droplets of rhGH solution on top of a commercial suitable backing liner in a predetermined pattern, also termed hereinafter "printing", following by drying at room temperature.

Printing of rhGH solution was carried out with a microliter syringe, fitted with blunt needle. The printing was performed using a digital controlled XYZ dosing machine, controlled by Basic program for the predetermined pattern of 144 microliter sized droplets, in a 12×12 array. Total printing area was 1.44 cm$^2$.

a. Preparation of rhGH Solutions rhGH solutions at various concentrations, from 8.8 mg/ml to 17.6 mg/ml, were prepared by dissolving GENOTROPIN® in deionized water. Each solution was transferred to a 100 µl syringe and air bubbles from the syringe were removed.

b. Printing the rhGH Solutions

For the preparation of a patch with the required amount of rhGH the volume of each droplet was calculated according to the concentration of the rhGH in the solution and accordingly the syringe's plunger displacement which is required per one droplet printing was adjusted, wherein the range of 0.035-

Figure 8:
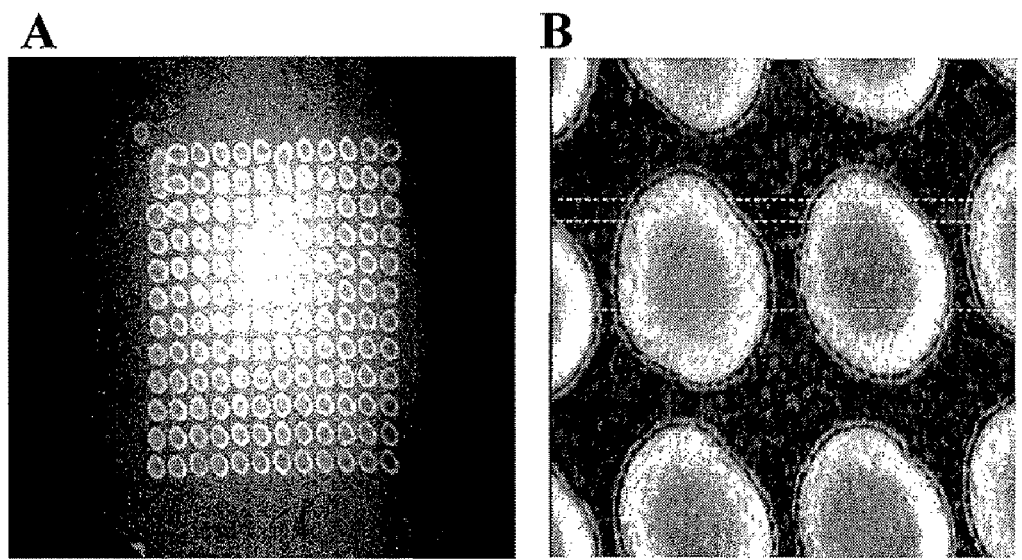
FIGS. 8A and B are views of a printed patch with FIG. 8B showing at a higher magnification.

0.105 mm corresponded to 0.09-0.18 μl. This range of displacement was fed into a Basic program that controls the printing. Next, the Backing layer film (DOW BLF2080™, The Dow Chemical Company, MI, USA) was placed flat with the bright side up on a flat metal block. The syringe containing the rhGH solution was loaded into the XYZ dosing machine, which then placed measured rhGH drops on the backing liner. It should be noted that within a few minutes the drops started to dry consecutively. Once the 144 dots array of printed droplets was formed the printing of new array started on a new position. According to this procedure it was possible to form up to 6 arrays on a 5.5×1.6" backing liner. Sections, 2×2 cm$^2$, of the printed 144 dotted arrays (e.g. FIG. 8) were kept at 4° C. in close vials.

Example 2

Preparation of rhGH Powder-Patches Using Non-Uniform Liners

The aim of the experiment is to create patches in which the pharmaceutically active powder is uniformly dispersed over a liner. In this experiment a polyester screen was used as a liner. Powder rhGH patches were prepared by applying 10 μl of rhGH solution (18.5 μg/μl) over pieces (15×15 mm$^2$, 7.7 mg) of polyester screen (mesh of 45 μm and 39% open area) following drying by air. This procedure was repeated 5 times for each preparation. FIG. 1 represents a screen containing 0.5 mg of rhGH, which was dispersed over the screen. The figure indicates that in this preparation most of the rhGH powder was located at the rim of the grid rather than being uniformly distributed.

Figure 2:
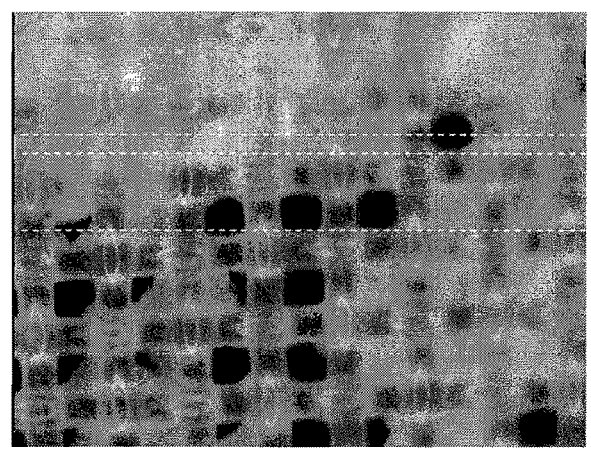
FIG. 2 is an image of a commercial diluted rhGH dried solution air-dried over a polyester screen.
Figure 3:
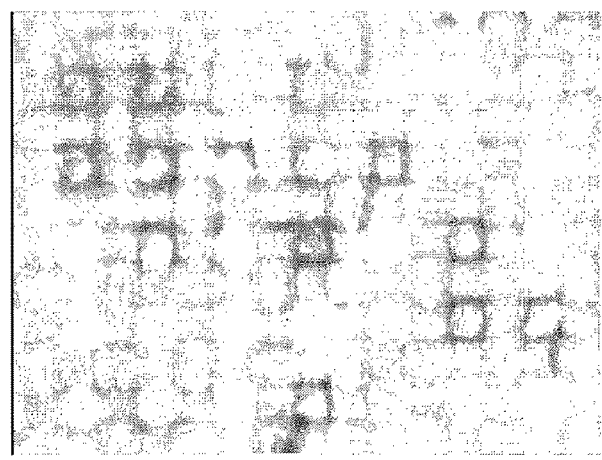
FIG. 3 is an image of mannitol mixed with methylene blue solution air-dried over a polyester screen.

To test the deposition of large amounts of hydrophilic agent on this type of polyester screens a diluted rhGH solution was used. A few drops of the diluted rhGH solution were applied on pieces of the polyester screen following air-drying. The powder that was attached to the screen after this procedure was not uniformly distributed as shown in FIG. 2. In order to emphasize the image of the powder-pattern that is left on the screen after this procedure, a mixture of mannitol and Methylene Blue was applied over a polyester screen (dark lines in FIG. 3).

Figure 4:
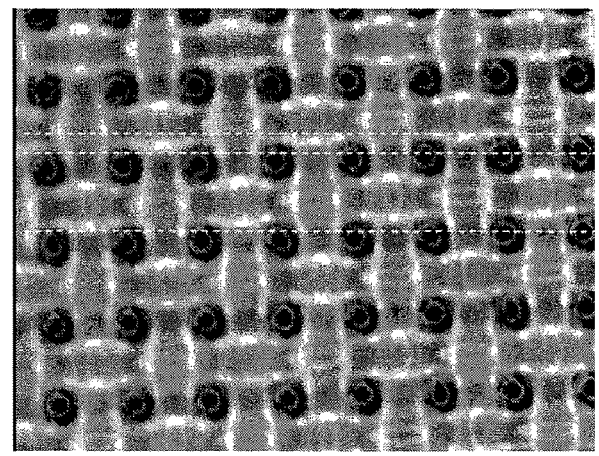
FIG. 4 is an image of sucrose solution air-dried over a polyester screen.

In order to examine whether increased powder load contributes to uniform distribution of the powder that is left after the water evaporates dry patches were prepared with sucrose instead of a drug. Square pieces of polyethylene screen (15× 15 mm$^2$, 7.8 mg, mesh of 45 μm and 39% open area) were immersed in a solution of 50% sucrose (commercial grade) following agitation of the screen to remove air entrapped within the screen pieces. Screen pieces were dried to remove excess sucrose solution. Dry sucrose was shown to fill evenly the square holes in the screen (FIG. 4).

Figure 5:
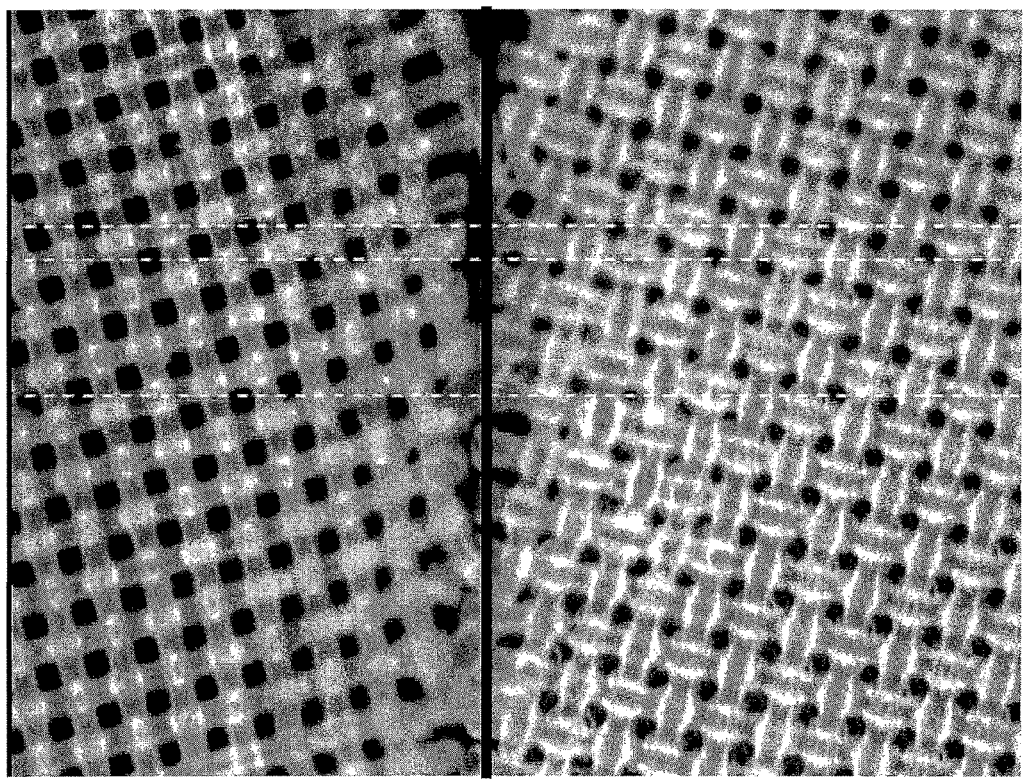
FIG. 5 is a composite of images of a polyester screen before (left panel) and after (right panel) the screen was immersed in sucrose solution and air-dried.

The total weight of the sucrose-loaded screen was 10.3 mg corresponding to 2.5 mg sucrose, which is 32% of the screen's initial weight. FIG. 5 represents images of a polyester screen before (left panel) and after (right panel) immersing in sucrose solution and drying. The uniform distribution of the dried sucrose is clearly observed in this figure (right panel).

Example 3

Transdermal Permeation of Powder rhGH Using ViaDerm Micro-Channeling Technology in Hypophysectomized Rats—Blood Levels and Protein Activity Materials and Methods
Animals: Rats, males, 250 gr, Sprague Dawley, hypophysectomized at Harlan USA labs. In order to minimize the damage caused by the hypophysectomy the animals were treated with thyroxine sodium salt (ELTROXIN™, Glaxo GmbH, Bad Oldesole, Germany) and HYDROCORTISONE from arrival until the start of the trial.

Test article: The dried fraction of GENOTROPIN® (rhGH and mannitol) was used for the transdermal applications. This fraction was spread on a hypoallergenic clear medical tape (Kendall Curity®, Emergency Medical Products Inc., USA) in doses specified below, and placed directly onto the skin as a transdermal patch. For the subcutaneous treatments, reconstituted GENOTROPIN® was used.

Experimental setup: 24 rats, given food and drink (0.45% NaCl in water) ad libitum, were divided into 4 groups of 6:
Group 1: ~0.8 mg/rat rhGH transdermal patch on ViaDerm treated skin.
Group 2: ~0.8 mg/rat rhGH transdermal patch on intact skin.
Group 3: Subcutaneous (SC) injection of rhGH, 150 μg/rat (0.33 ml/rat).
Group 4: Untreated.

The transdermal groups (1 and 2) received a treatment including: Shaving, drying, baseline Trans Epidermal Water Loss measurement (TEWL; DERMALAB® Cortex Technology, Hadsund, Denmark), two ViaDerm applications of 200 micropores/cm$^2$ (placebo for Group 2), second TEWL measurement and patch application. At the end of the study all animals were sacrificed by an IV overdose of sodium-pentobarbital (140 mg/kg).

ViaDerm parameters: burst length—500 μsec, starting amplitude—250 V, number of bursts—5 and applications per site—2 (200 micropores/cm$^2$).

Blood sampling: Blood samples (0.5 ml/rat) were withdrawn at 6 time points, t=0, 2, 4, 6, 12 and 24 hours, from the tail end of anesthetized rats (20 mg/rat ketamine, intramuscular).

Serum analysis: rhGH in the serum was detected using an Elisa kit (DSL-10-1900; Diagnostic Systems Laboratories, TX, USA) specific for rhGH. The kit does not detect endogenous rat GH. IGF-1 was detected according to RIA protocol (Endocrine, Vol. 16, no. 1, 1-6, Oct. 2001). Utilizing this detection protocol it is impossible to distinguish between IGF-1 synthesis which is regulated by endogenous GH to IGF-1 synthesis that is regulated by exogenous GH.

Results
1. rhGH in the Serum

Figure 6:
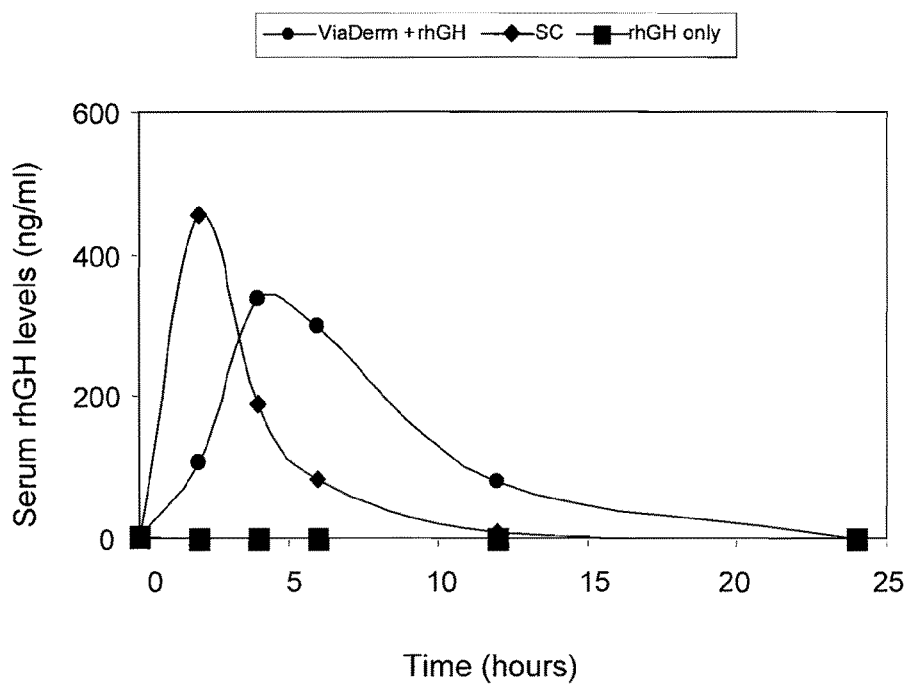
FIG. 6 exhibits the levels of rhGH in the serum of rats.

The average concentrations of rhGH in the serum are plotted in FIG. 6. Group 1 (ViaDerm+rhGH) demonstrated an average profile with a peak at 4 hours post administration. This peak was lower and was achieved later than the maximal concentration of rhGH in the SC group (Group 3). Groups 2 (rhGH on untreated/intact skin) and 4 (no treatment) demonstrated negligible concentrations of rhGH in the serum as expected. In Group 3 (subcutaneous injection) 5 out of 6 rats demonstrated a typical injection profile with peak concentration 2 hours post injection and after 4 hours in the sixth rat. Although rhGH decayed in the serum of all rats in a similar pattern, the average values exhibited a large variance, larger than the variance observed in the ViaDerm treated group.

2. Pharmacokinetics—AUC Calculations for rhGH

AUC is defined as the area under the curve and is expressed in units of ng*hr/ml. The bioavailability was calculated relatively to the SC values according to the following formula:

$$(AUC_{group}/Dose_{group})/(AUC_{SC}/Dose_{SC})*100=\text{Bioavailability (\%)}.$$

ViaDerm treated group (Group 1)—3052 μg/hr/ml absolute AUC value, and 381.6 μg/hr/ml normalized AUC for 0.1 g rhGH.

SC group (Group 3)-1692 μg/hr/ml absolute AUC value, and 1128 μg/hr/ml normalized AUC for 0.1 g rhGH.

According to these calculations the ViaDerm treated group demonstrated a bioavailability value of 33.8% compared to the SC group. AUC values were improved with the use of lower doses of rhGH and increased uniformity of spread within the patches using printed patches as shown in the following example.

3. IGF-1 in the Serum

Figure 7:
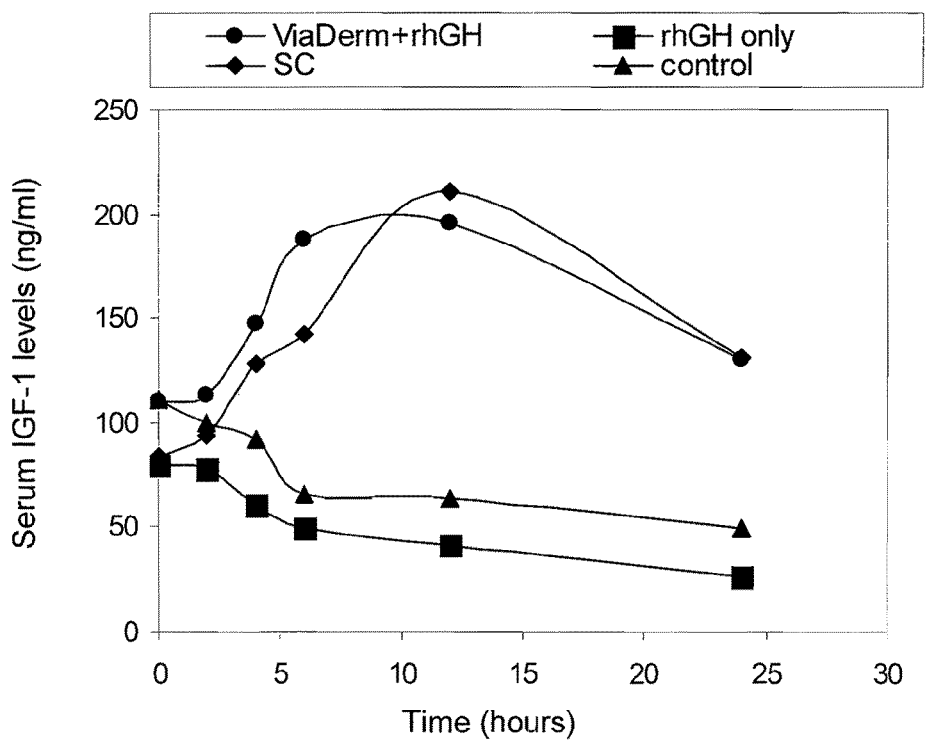
FIG. 7 shows IGF-I levels in the serum of rats.

The average concentrations of IGF-1 in the serum are plotted in FIG. 7. Group 1 (ViaDerm+rhGH treated) demonstrated elevation of IGF-1 indicating that the activity of rhGH is maintained using ViaDerm+rhGH powder patch system. The maximal average concentration was observed at 12 hours post treatment and between 6-12 hours post treatment for the individual rats. Group 2 (rhGH only) demonstrated low level of IGF-1 throughout the treatment period. This result was coherent with the low rhGH levels in the serum of this group (see FIG. 6). Group 3 (subcutaneous injection) demonstrated the anticipated elevation of IGF-1 with peak concentration at 12 hours post treatment for all rats on average and for each rat individually. These results were similar to IGF-1 levels in the ViaDerm+rhGH group (FIG. 7). Group 4 (no treatment) demonstrated an expected low level of IGF-1 throughout the treatment period verifying the results obtained for rhGH.

The similar activity in both the ViaDerm+rhGH group and SC groups could be further rationalized by the fact that the dose used in this study for the former group was very high (0.8 mg/patch), higher than the absorption capability of the rat. This may also lead to the AUC results achieved.

The foregoing example provides patches and methods for improving the accuracy of dosage per patch and the uniformity of spread on each patch.

Example 4

Bioavailability of rhGH Using Printed Patches and Via-Derm Micro-Channeling Technology in Hypophysectomized Rats Materials and Methods The materials and methods applied in this example were similar to those in EXAMPLE 3 except from the following points:

a) The animals were treated with ELTROXIN™ and hydrocortisone only until 10 days before initiating the treatments.
b) The test article was a printed patch of rhGH in two doses: 0.15 mg/patch and 0.5 mg/patch. The patches were composed of a backing liner (DOW BLF2080™, The Dow Chemical Company, MI, USA) on which drops of GENOTROPIN® were evenly placed. All the patches contained 144 drops over an area 1.4×1.4 $cm^2$. The printed patch was attached to the skin by a fixing patch, 2 cm×2 cm with 300 μm thick (wet) glue (DURO-TAK™ 3872516; National Starch & Chemical Pty Ltd, NSW, Australia) on the backing liner.
c) The experimental setup included 2 groups of 3 rats each:
Group 1: Treated with ViaDerm+one 0.15 mg printed patch.
Group 2: Treated with ViaDerm+one 0.5 mg printed patch.

Results

1. Printed Patches

Printed patches were produced in two doses, 0.15 mg and 0.5 mg of rhGH. An overview of a representative printed patch (FIG. 8A) and of individual printed dots within the patch (FIG. 8B) reveals a relatively uniform distribution of the dots. Patches from the same production batch were analyzed by HPLC to measure the actual quantity of rhGH per patch with respect to the anticipated quantity. rhGH concentration in the 0.15 mg printed patches was found 2-9% higher than expected and in the 0.5 mg printed patches 10-19% higher than expected.

2. rhGH in the Serum

TEWL results were all within the set limits, namely, pre-treatment TEWL levels were lower than 8.5 $g/h/m^2$ and TEWL differences before and after ViaDerm treatment were higher than 18 $g/h/m^2$.

Figure 9:
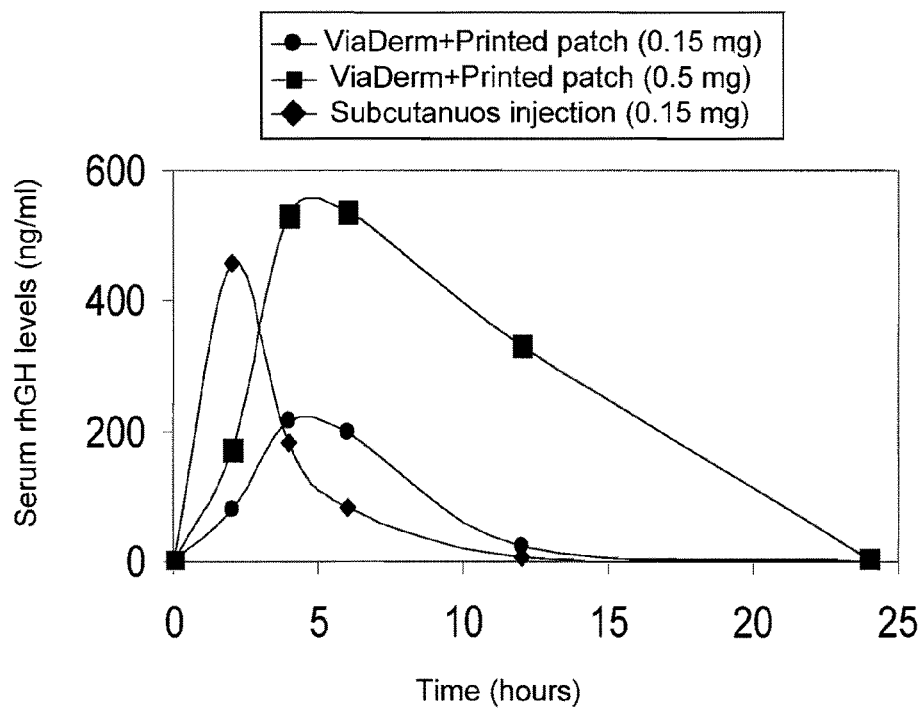
FIG. 9 shows the serum levels of rhGH, applied through transdermal printed patches and through subcutaneous injections.

Group 1 (ViaDerm+0.15 mg printed patch) demonstrated an average profile with a peak at 4 hours post administration (FIG. 9). Group 2 (ViaDerm treated+0.5 mg printed patch) demonstrated an average profile with a peak at 6 hours post administration. In both groups the results for 4 and 6 hours were high and similar. In Group 1 there was a considerable drop between 6 and 12 hours, while in Group 2 the high levels were maintained until 12 hours and the drop occurred between 12 and 24 hours post application. The two doses of printed patches demonstrated a significant difference in rhGH serum level per time point, indicating that these doses provided a satisfying experimental setup for verifying dose dependencies.

A comparison was carried out between sera levels of rhGH after application of rhGH printed patches and sera levels of rhGH after subcutaneous injection of rhGH (see Example 3), following ViaDerm treatment (FIG. 9). The peak achieved by subcutaneous injection appeared earlier than in the two groups of printed patches (2 hours). The peak concentration of subcutaneous injection was higher than the 0.15 mg printed patch group and lower than the 0.5 mg printed patch group.

Figure 10:
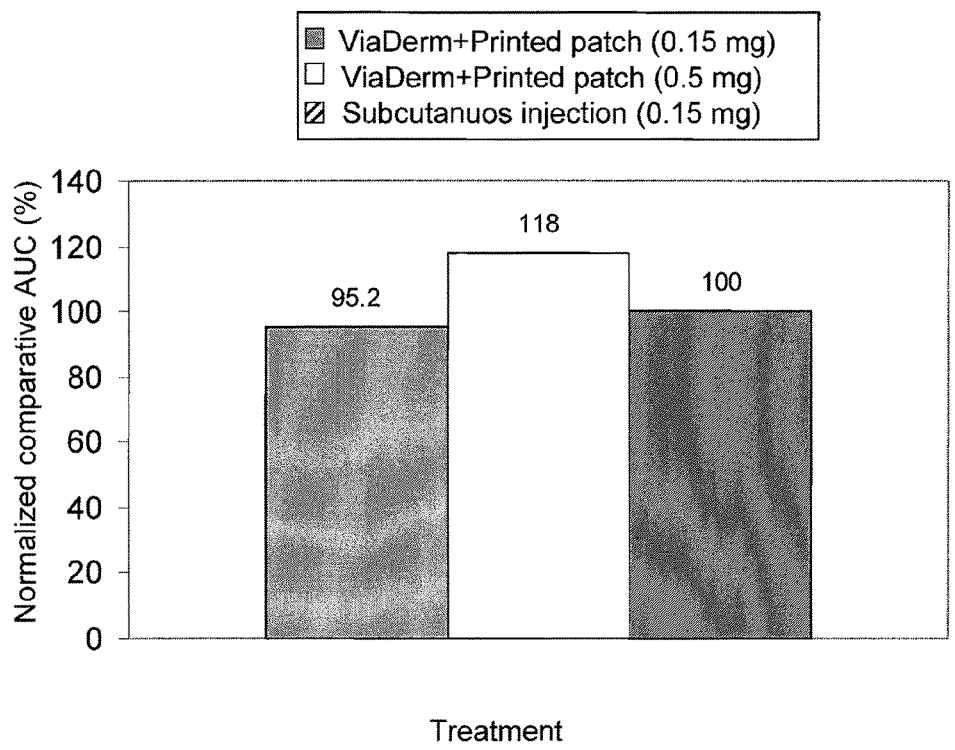
FIG. 10 presents AUC values normalized to administration of 0.1 mg rhGH.

3. Pharmacokinetics:

Representative AUC values normalized to administration of 0.1 mg rhGH, wherein 100% refers to SC injection, are shown in FIG. 10. AUC values for each group treated with rhGH in the previous example and the current one were as follows:

a) Group 1 (ViaDerm+0.15 mg printed patch) 1594 ng-hr/ml absolute value, 1063 μg-hr/ml normalized to 0.1 mg rhGH.
b) Group 2 (ViaDerm+0.5 mg printed patch) 6563 ng-hr/ml absolute value, 1313 μg-hr/ml normalized to 0.1 mg rhGH
c) Group 3 of Example 3 (SC injections of 0.15 mg/rat)- 1692 ng-hr/ml absolute value, 1128 μg-hr/ml normalized for 0.1 mg rhGH.

According to these calculations Group 1 of the printed patches demonstrated a bioavailability value of 95.2% compared to the SC injections group and Group 2 of the printed patches demonstrated a bioavailability value of 118% compared to the SC injections group. These results, therefore, indicate a higher delivery rate and a higher bioavailability rate using rhGH-printed patch compared to rhGH-powder patch.

Example 5

Bioavailability of rhGH Printed Patches Using ViaDerm Micro-Channeling Technology in Normal Rats and Guinea Pigs Instruments and Materials ViaDerm micro-channeling apparatus was used. The density of the microelectrode array used in these studies was 100 microelectrodes/$cm^2$. The device was applied twice on each location, so the density of the micro channels was 200/$cm^2$. The skin was treated with an applied voltage of 330V, frequency of 100 kHz, two bursts, 700 microsecond burst length, and no current limitation.

In Vivo hGH Transdermal Delivery

Male Guinea pigs (500-800 grams, Dunkin Hartley, Harlan laboratories Ltd., Israel) and Male rats (350-400, Sprague Dawley, Harlan laboratories Ltd., Israel), were premedicated with IP injections of 10% ketamin/2% xylazine solution at a ratio of 70:30, 1 ml/kg. Anesthesia was maintained with either isofluorane or halothane gas. The abdominal skin hair was shaved carefully, and was cleaned with isopropyl alcohol. After 30 min, transepidermal water loss measurements (TEWL, Dermalab Cortex Technology, Hadsund, Denmark) were performed to check skin integrity. Skin micro channeling was performed by the use of the ViaDerm instrument with the conditions described above. TEWL was then measured again to control the operation. The treated skin was covered with the rhGH patches and blood samples were withdrawn from a preinserted carotid cannula in guinea pig or from the rat's tail at predetermined times post application. The serum was separated by centrifugation and analyzed for rhGH by Elisa kit (DSL-10-1900, Diagnostic Systems Laboratories, Inc. Webster, Tex., USA). The transdermal delivery of rhGH was compared to that of subcutaneous hGH delivery.

Results

1. Transdermal Delivery and Bioavailability in Rats

Figure 11A:
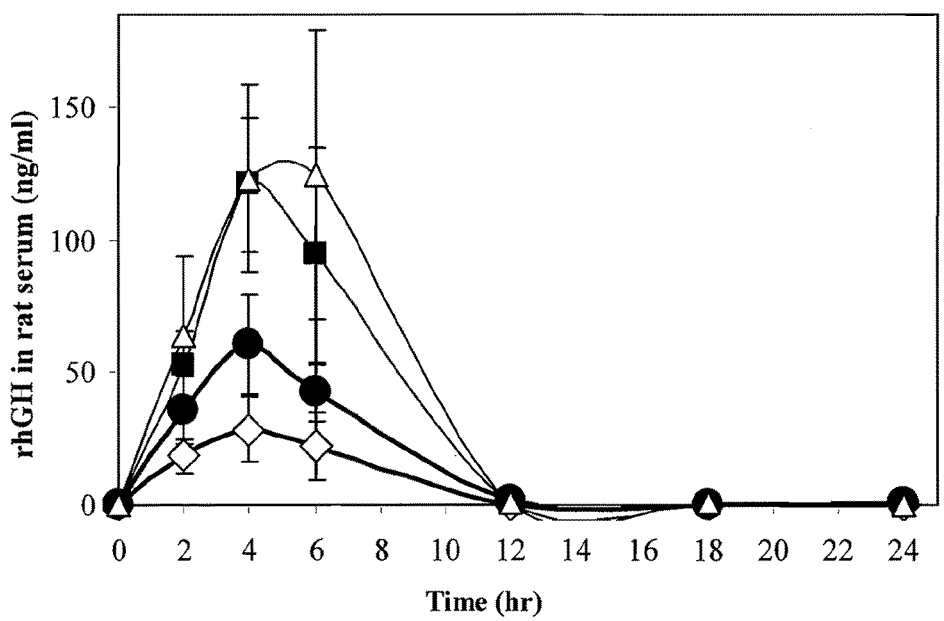
FIGS. 11A and B show the rhGH blood levels following transdermal application of rhGH-printed patches on ViaDerm treated skin area. (A), Serum levels (ng/ml) in rats; rhGH amounts printed on a patch were as follows: 75 µg (◇); 150 µg (●); 300 µg (■); and 400 µg (△); (B) Plasma levels (ng/ml) in guinea pigs; rhGH amounts printed on a patch were as follows: 50 µg (◇); 150 µg (●); 300 µg (△); and 400 µg (■).

Recombinant hGH blood levels in rat serum following transdermal application of hGH-printed patches on ViaDerm treated skin are shown in FIG. 11A. A dose dependant rhGH blood profile was observed at patch concentrations of 75-300 µg. An utmost effective dosage of 300 µg seems to be optimal since administration of higher concentrations of rhGH did not result in a significant increase in its blood levels (see FIG. 11A).

AUC and relative bioavailability values are shown in Table 1. The bioavailability of rhGH following transdermal delivery was high (75% relative to subcutaneous (SC) administration). AUC values increased with the increase of the rhGH amount in the patch, while the bioavailability remained at the same values (about 75% of that of SC administration) at rhGH amount range of 75-300 µg.

TABLE 1

AUC and bioavailability values in rats.

| Mode of Delivery | Dose (µg) | AUC (ng * hr/ml) | Bioavailability (% of SC) |
|---|---|---|---|
| SC | 150 | 489 | 100 |
| Transdermal | 75 | 184 | 75.3 |
| Transdermal | 150 | 376 | 76.9 |
| Transdermal | 300 | 727 | 74.3 |
| Transdermal | 450 | 884 | 60.3 |

2. Transdermal Delivery and Bioavailability in Guinea Pigs

Figure 11B:
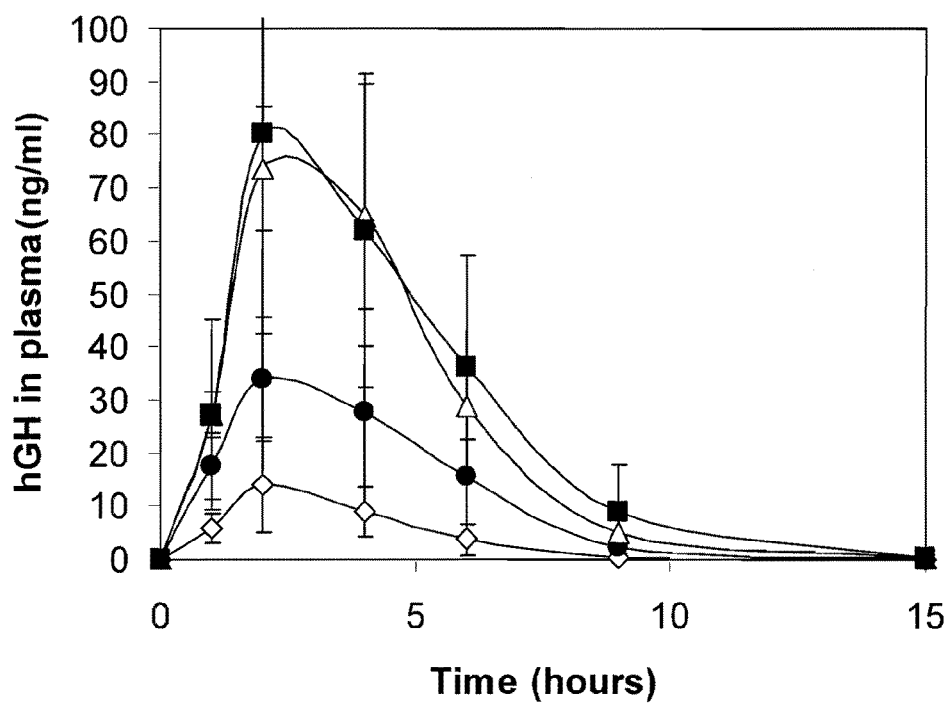

Recombinant hGH blood levels in guinea pigs plasma following transdermal application of rhGH-printed patches on ViaDerm treated skin are shown in FIG. 11B. Similar to rat, a dose dependant rhGH blood profile was observed at patch concentrations of 50-300 µg. The highest effective dosage of 300 µg was found to be optimal also in guinea pigs since administration of higher concentrations of rhGH did not result in a significant increase in its plasma levels (see FIG. 11B).

AUC and relative bioavailability values are shown in Table 2. The bioavailability of rhGH in guinea pigs following transdermal delivery was about 30% relative to SC administration. AUC values were found to be dose dependent while the bioavailability remained at the same values. The differences in the bioavailability values between rat and guinea pig could be attributed to specific proteases in each animal, differences in skin receptors for rhGH, absorption to extracellular matrix components, differences in clearance parameters, different reactions to SC injections, and alike.

TABLE 2

AUC and bioavailability values in guinea pigs.

| Mode of Delivery | Dose (mg) | AUC (ng * hr/ml) | Bioavailability (% of SC) |
|---|---|---|---|
| SC | 50 | 176 | 100 |
| Transdermal | 50 | 57 | 32.4 |
| Transdermal | 150 | 175 | 33.1 |
| Transdermal | 300 | 362 | 34.3 |
| Transdermal | 400 | 404 | 28.7 |

Example 6

Transdermal Delivery of Insulin Using Printed Patches and ViaDerm Technology in Diabetic Rats Instruments and Materials ViaDerm apparatus was used. The density of the microelectrode array used in these studies was 100 microelectrodes/cm$^2$. The device was applied twice on each location, so the density of the micro channels was 200/cm$^2$. The skin was treated with an applied voltage of 330V, frequency of 100 kHz, two bursts, 700 microsecond burst length, and no current limitation.

Keto-Diastix-Glucose and Ketones urinalysis sticks, GLUCOMETER®, and blood glucose test strips were used (Ascensia Elite, Bayer). Blood glucose test strips Norm: 75-108 mg/dl (lot no. A2G05EC072).

Streptozotocin (STZ) was obtained from Sigma (Sigma, St. Louis, Mo., USA). The human recombinant insulin HUMULIN® (regular-100 IU/ml) and HUMALOG® (Lispro-100 IU/ml) were purchased from Lilly (Lilly France S.A., Fegershein, France).

Printed Patch Preparations

Printed patches that contained insulin were prepared as described for the rhGH printed patches (see EXAMPLE 1).

Bioactivity of Insulin in Diabetic Rats

Male rats (300-325, Sprague Dawley, Harlan laboratories Ltd., Israel) were deprived of food and received water as libitum 48 hr prior to patch applications. Streptozotocin (55 mg/kg in citric buffer, 0.1 M, pH 4.5) was injected intraperitonally (IP) to the rats 24 hr prior to patch applications in order to induce diabetes. The rats were considered diabetic if 24 hours following streptozotocin injections the glucose levels were above 300 mg/dl, urine glucose was found to be positive and urine ketones were found to be negative. The diabetic rats were premedicated with IP injections of 10% ketamin/2% xylazine solution at a ratio of 70:30, 1 ml/kg. Anesthesia was maintained with either isofluorane or halothane gas. The abdominal skin hair was shaved carefully, and was cleaned with isopropyl alcohol. After 30 min, transepidermal water loss measurements (TEWL, Dermalab Cortex Technology, Hadsund, Denmark) were performed to check skin integrity. Skin micro-channeling was performed by the use of the ViaDerm instrument with the conditions described above. TEWL was measured again to control the operation. The treated skin was covered with Lispro (HUMALOG®) or Regular (HUMULIN®) 1.5 IU insulin-printed patches. SC injections of 0.4 IU served as a positive control.

Blood samples were withdrawn from the tip of the rat's tail at 0, 2, 4, and 6 hr post application, and glucose level was determined.

Results

Bioactivity of Insulin in Diabetic Rats

Figure 12:
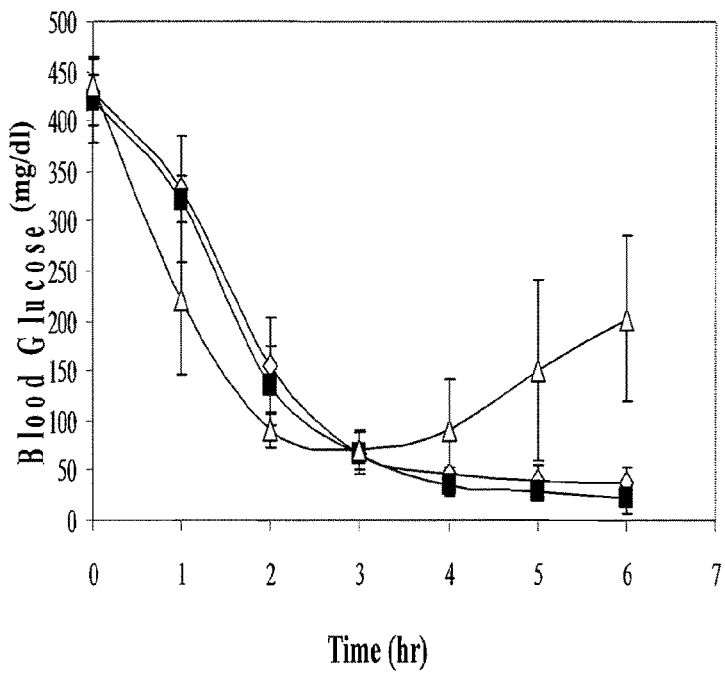
FIG. 12 shows blood glucose levels following transdermal application of insulin-printed patches on ViaDerm treated skin area and following subcutaneous insulin application Transdermal delivery of insulin Humulin® R (Regular) (◇), Humalog® (Lipro) (■); Subcutaneous insulin administration (△).

Blood glucose levels following the application of insulin-printed patches to micro-channeled skin of diabetic rats are shown in FIG. 12. No differences in glucose blood profile were observed between the HUMALOG® and HUMULIN® printed patches. Three hours following patch application the levels of glucose decreased from about 400 mg/dl to about 70 mg/dl in both the SC and printed patches experimental groups. Glucose levels begun to increase 4 hr following SC administration of insulin and reached levels of about 200 mg/dl after 6 hr, while the levels of glucose continue to decrease after 4 hr following patch application and reached levels of about 30 mg/dl after 6 hr. It should be noted that normal blood glucose level in rats is in the range of 100-200 mg/dl. It, therefore, suggests that the optimal dose of insulin in printed patches for diabetic rats should be lower than 1.5 IU in order to receive similar effect as of the SC injection. Thus, our findings show a novel, efficient, and painless way for insulin administration in diabetic rats.

Example 7

Stability of rhGH in Printed Patches: Effect of Various Formulations

It is advantageous that patches aimed at transdermal drug delivery would exhibit long-term stability for prolonged shelf life. In order to find out the optimal formulation for rhGH to be printed on a patch, rhGH was prepared in various formulations, printed on patches as described in EXAMPLE 1, and then the stability of rhGH in each of the rhGH-printed patches was checked at several storage temperatures.

Instruments and Materials

Various formulations of commercial rhGH, GENOTROPIN® (5.3 mg/16 IU, Pharmacia and Upjohn, Stockholm, Sweden), were prepared as follows: All the formulations contained 200 μg of rhGH. Sucrose, D(+) trehalose, pluronic 127, Tween 20, human serum albumin, PEG 6000, histidine, and poloxamer 188 were used as excipients in the various formulations. The various excipients were mixed with rhGH (see Table 3 for mixing ratios), and then printed on Dow film backing liner (DOW BLF 2080™ 3 mm) and packed as described in EXAMPLE 1. The various rhGH patches were kept at −18° C., 4° C., and at RT.

HPLC Analysis

The stability testing was performed according to the pharmacopoeial method (European Pharmacopoeia, $4^{th}$ edition, 2002. Somatropin 01/2002:0951, p. 1937-1939). At time points of 0, 1, 2, and 3 months, rhGH was extracted to a phosphate buffer solution (0.025 mM), and the solution was analyzed for rhGH amount, and for the presence of high MW protein aggregates and dimers. The analysis of high MW protein aggregates and dimers was conducted by size exclusion (SE) HPLC using TSK gel G2000 SWxl (30 cm×Ø 7.8 mm, 5 μm), and Pre-column-TSK-Gel (6 cm×Ø 6 mm). The mobile phase was phosphate/2-propanol solution (97 volumes of 0.063 M Buffer phosphate pH 7.0, and 3 volumes of 2-propanol), and the detection was performed at 214 nm. The solution was also analyzed for other impurities and degradation products by reversed phase (RF) HPLC using C4 column and a mobile phase of 0.05M Tris-hydrochloride buffer solution, pH 7.5. The detection of degradation products was performed at 220 nm.

The limit amounts allowed for impurities and degradation products according to the European Pharmacopeia is 6% and 13% when measured by the SE-HPLC and RF-HPLC, respectively.

In Vivo rhGH Transdermal Delivery—Bioavailability Test

Male Guinea pigs (500-800 grams, Dunkin Hartley, Harlan laboratories Ltd., Israel) were premedicated with IP injections of 10% ketamin/2% xylazine solution at a ratio of 70:30, 1 ml/kg. Anesthesia was maintained with either isofluorane or halothane gas. The abdominal skin hair was shaved carefully, and was cleaned with isopropyl alcohol. After 30 min, transepidermal water loss measurements (TEWL, Dermalab Cortex Technology, Hadsund, Denmark) were performed to check skin integrity. Skin micro-channeling was performed by the use of the ViaDerm apparatus with the following conditions: The skin was treated with an applied voltage of 330V, frequency of 100 kHz, two bursts, 700 microsecond burst length, and no current limitation. The density of the microelectrode array used in this study was 100 microelectrodes/$cm^2$. The device was applied twice on each location, so the density of the micro-channels was 200/$cm^2$. TEWL was then measured again to control the operation. The treated skin was covered with the rhGH-printed patches and blood samples were withdrawn from a preinserted carotid cannula at the following times post application 0, 2, 4, 6, 9, 12, and 15 hr. The serum was separated by centrifugation and analyzed for rhGH by Elisa kit (DSL-10-1900, Diagnostic Systems Laboratories, Inc. Webster, Tex., USA). The delivery of rhGH in printed patch without additives was compared to that of rhGH in printed patch containing sucrose or trehalose.

Results

Stability

A high correlation was found between the analysis of rhGH amount in the patches and the amount of impurities and degradation products. The results of a stability study of patches containing rhGH without additives are summarized in Table 3. As shown in Table 3, after three-month storage at −18° C., the amount of dimers and aggregates that was found in the extracted solution was insignificant (0.1%), and the amount of other impurities and degradations products leveled only to 1.2%. Storage of the printed patches at 4° C. and at 22° C. led to a minor formation of impurities and degradation products, which were found to be less than the allowed levels (see Table 3). These stability findings suggest that the favorable storage temperature for printed patches containing rhGH without additives is 4° C.

The results of a stability study after three-month storage of printed patches that contained various rhGH formulations are summarized in Table 4. Stability was also checked at earlier times. Storage at −18° C. and 4° C. revealed high stability regardless of the formulation used. However, storage at room temperature of rhGH-printed patches wherein rhGH was prepared in formulations that contained either Tween 20 or PEG 6000, resulted in rhGH instability relative to that observed in the rhGH control printed patch. The total amount of aggregates and dimers in rhGH formulations that contained Tween 20 or PEG 6000 was found to be 8.5% in each case (Table 4). Recombinant hGH-printed patches wherein rhGH was prepared in formulations that contained either sucrose or trehalose were shown to be more stable than the control rhGH-printed patch. This is indicated by the observation that storage at 22° C. of printed patches of rhGH formulated in either sucrose or trehalose resulted in the lowest level of impurities and degradation products.

Bioavailability

Figure 13:
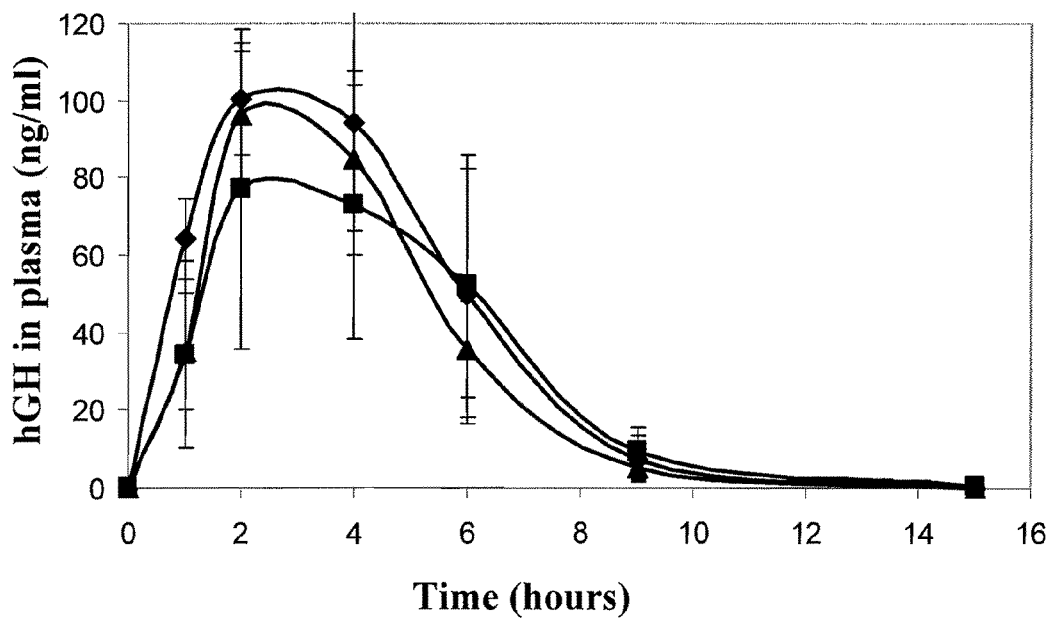
FIG. 13 shows the delivery of rhGH through ViaDerm treated guinea pig skin using printed patches in which rhGH was prepared in formulations containing either sucrose (●), trehalose (■), or none (△).

Delivery of rhGH through ViaDerm treated guinea pig skin is shown in FIG. 13. As shown in FIG. 13, similar bioavailability was observed following the delivery of rhGH in printed patch without additives and following the delivery of rhGH in printed patch that contained sucrose. Delivery of rhGH in printed patch that contained trehalose as an excipient resulted in an insignificant decrease in the rhGH bioavailability (FIG. 13). As the use of sucrose and trehalose in rhGH formulations did not hamper the rhGH bioavailability, but increased rhGH stability, these findings indicate that it is advantageous to include these sugars in rhGH formulations.

Example 8

ViaDerm Device: Specifications and Performance In Vivo

Figure 14:
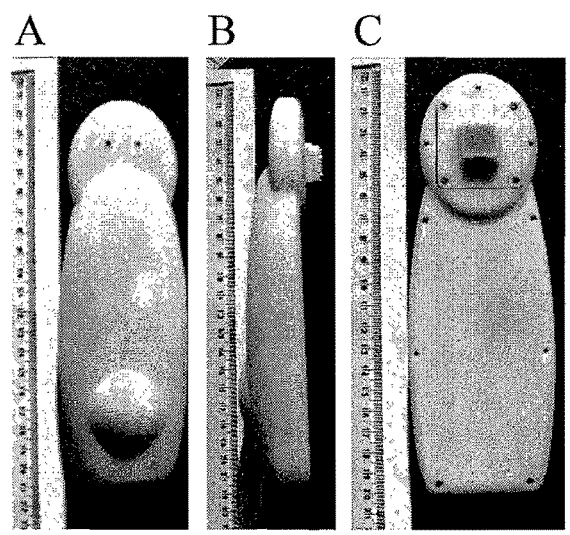
FIGS. 14A, B and C exhibit top (A), side (B) and bottom (C) views of the control unit of a ViaDerm device.
Figure 15:
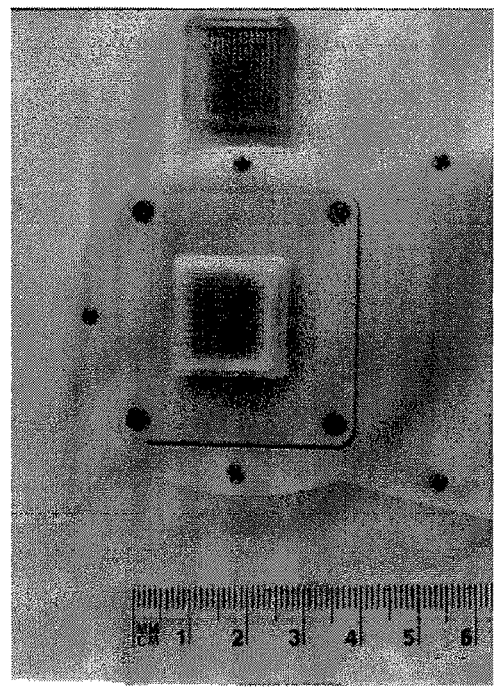
FIG. 15 is a photograph of the microelectrodes array utilized to create micro-channels in the skin.

The ViaDerm apparatus that was used to generate micro-channels in the pre-clinical and clinical studies described herein is disclosed in U.S. Pat. No. 6,148,232 and International Patent Applications WO 02/085451 and WO 02/092163. In brief, ViaDerm is comprised of the following:
1. A reusable main unit comprising a control unit, which generates an RF electrical current (FIG. 14).
2. A disposable electrode cartridge (FIG. 15) comprising an array of microelectrodes attached onto the end of the main unit.

Figure 16:
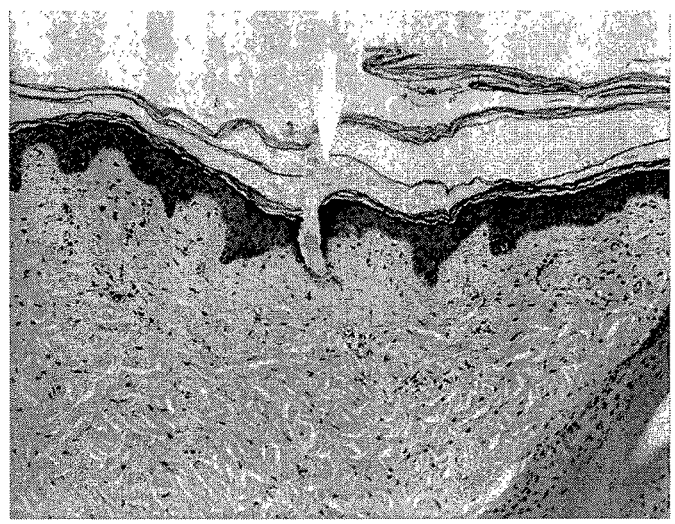
FIG. 16 is a hematoxylin and eosin stained histological section of porcine ear skin treated by ViaDerm.

Histological studies of micro-channels formed by ViaDerm within a porcine skin showed that the dimensions of the micro-channels are controllable and precise: each micro-channel was 30 μm in width and 50-100 μm in depth. In the porcine skin, wherein the epidermis depth is about 40 μm, these micro-channels penetrated into the dermis. However in humans, in whom epidermis depth is about 100 μm, such micro-channels reside within the limits of the epidermis. In addition, it should be noted that the micro-channels were very localized, and the skin surrounding the micro-channels maintained its normal structure (FIG. 16).

Figure 17:
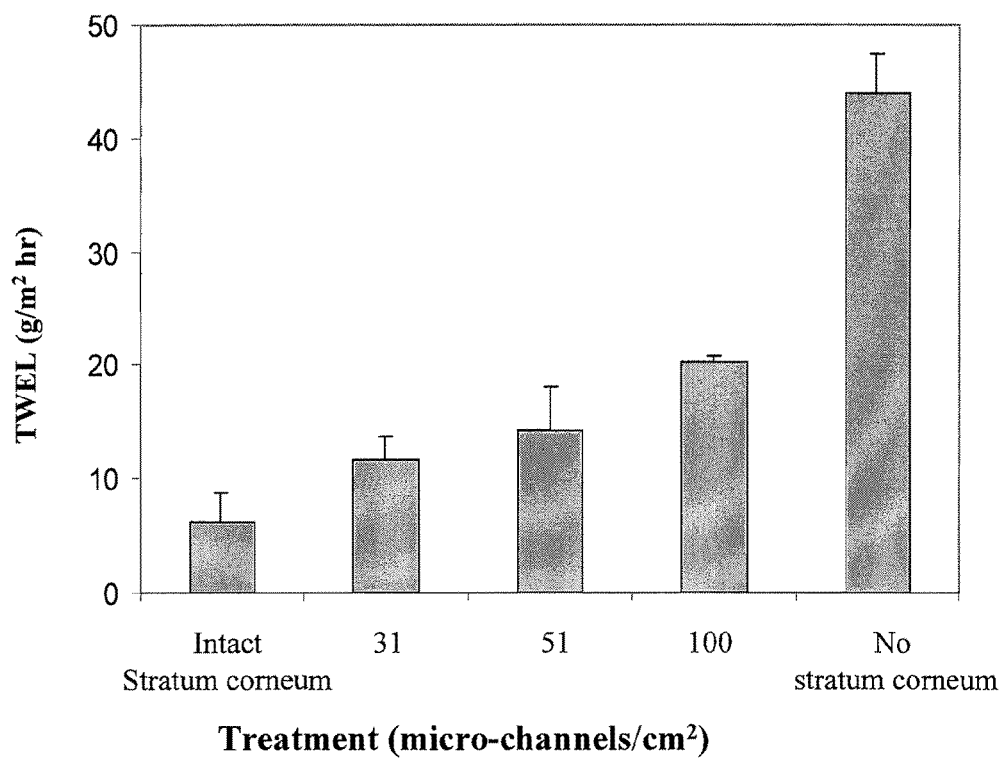
FIG. 17 presents the transepidermal water loss (TEWL) from porcine ear skins, after generation of micro-channels or after removal of the stratum corneum.

TEWL was measured in skin sections of porcine ear after generating different quantities of micro-channels (FIG. 17). TEWL linearly increased with increasing the number of micro-channels.

Example 9

Clinical Studies of ViaDerm Performance

Materials and Methods
Study subjects. ViaDerm performance was assessed by a study conducted with twenty healthy, adult volunteers, 10 males and 10 females. The study was conducted at ClinRx a Clinical research organization under Good Laboratory Practice (GLP) standards. Each subject received 10 treatments, in a randomized manner such that a given treatment was applied to different subjects and/or in each subject at different sites.
Treatment protocol. The treatment sites were the inner arm and hand. Each treatment included the following steps: preparing the skin (cleaning); measuring TEWL ($T_{0-}$) at a treatment site and at an adjacent site; placing ViaDerm upon the treatment site and activating the electrodes with controlled RF electrical energy; measuring TEWL immediately at the treatment site and the adjacent site; Scoring for erythema, edema and tolerability ($T_{0+}$), at the treatment site; covering the treatment site with a sterile hydrogel (VIGILON™, The Medical Supply Company Inc., NY, USA) patch; Removing the patch at T=24 hr; measuring TEWL at the treatment site and at the adjacent site; Scoring for erythema and edema at the treatment site at T=25 hr and 48 hr.

ViaDerm performance. Measuring Transdermal Water Loss (TEWL) at a skin site treated with ViaDerm in comparison to an adjacent untreated skin assessed formation of micro-channels. Safety of ViaDerm was evaluated by measuring irritation (erythema and edema) at the treatment site using a scale of zero to eight in accordance with Draize irritation index (Table 5). The response to irritation induced by ViaDerm was assessed by a Cumulative Irritation Index (Table 6). Skin tolerability was studied by measuring pain on a 100 mm Visual Analog Scale (VAS) following ViaDerm treatment.
Results
a. Safety Evaluation.
Erythema was observed at sites treated with ViaDerm and covered with a patch for 24 hr. This erythema disappeared 24 hr after removal of the patch. Erythema was not observed in non-treated adjacent sites. The maximal mean value of erythema was 0.81 accounting for a very slight erythema according to Table 5. The different application sites exhibited similar irritation scores.

Edema was observed at sites treated with ViaDerm and covered with a patch for 24 hr. This edema disappeared 24 hr after removal of the patch. Edema was not observed in non-treated adjacent sites. The maximal mean value of edema was 0.25 accounting for negligible edema according to Table 6. The different application sites exhibited similar irritation scores.

The maximal mean combined irritation index (erythema and edema) was 0.75 for the ViaDerm treatment sites when occluded and 0.5 for the adjacent non-occluded sites accounting for a minor response.

TABLE 5

Draize irritation index.

| | Grade |
|---|---|
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beet redness) to eschar formation preventing grading of erythema | 4 |
| Edema formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |
| Total possible score for irritation | 8 |

TABLE 6

Cumulative Irritation Index.

| Response category | Mean Score |
|---|---|
| Negligible | 0 to 0.4 |
| Slight | 0.5 to 1.9 |
| Moderate | 2.0 to 4.9 |
| Severe | 5.0 to 8.0 | b. Tolerability Evaluation
Pain scores were in the range of 0-50 mm. The pain score per subject was an average from 10 ViaDerm applications.

The average values (per site of treatment) ranged from 2.1 mm to 7.02 mm. Those values are considered negligible.

Example 10

Transdermal Delivery of Salmon Calcitonin in Pigs

The aim of this study was to compare the bioavailability of salmon calcitonin (sCT) applied transdermally in printed patches to the bioavailability of the hormone injected subcutaneously.

Pigs (males, 10-12 kg, Large white) were treated as follows:

Group 1: 1 ml of salmon calcitonin containing 16.7 µg peptide (Miacalcin, Novartis Pharma Ag, Basle, Switzerland) was injected subcutaneously (S.C) to each pig (total 3 pigs).

Group 2: Each pig underwent 2 ViaDerm applications on one site on the back (150 micro-channels per cm$^2$). Patches of 400 µg sCT/patch of 1.4 cm$^2$ were placed on the treated area (total 3 pigs).

Group 3: Each pig underwent 2 ViaDerm applications on one site on the back (150 micro-channels per cm$^2$). Patches of 200 µg sCT/patch of 1.4 cm$^2$ were placed on the treated area (total 3 pigs).

In order to determine sCT concentrations in pig plasma an ELISA assay was performed (Diagnostic Systems Laboratories, Inc. Webster, Tex., USA).

Figure 18:
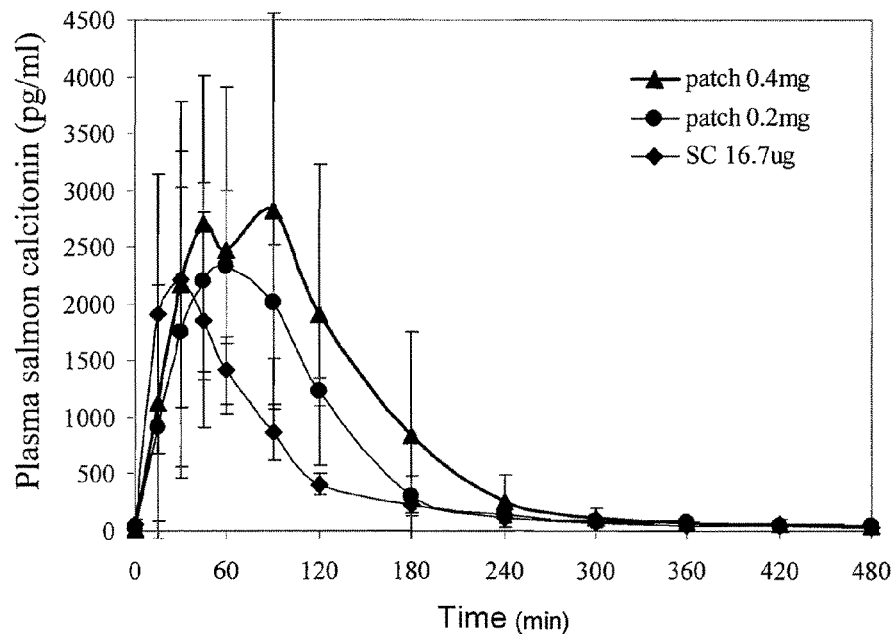
FIG. 18 shows the concentration of salmon calcitonin (sCT) in pigs after subcutaneous injection or transdermal delivery of sCT. sCT-printed patches containing 200 or 400 µg sCT were applied on ViaDerm treated skin of pigs and the plasma concentration of sCT as a function of time was measured. As a control, pigs were injected subcutaneously with sCT and the plasma concentration of sCT was measured.

FIG. 18 shows the plasma concentrations of sCT after subcutaneous injection (Group 1) or transdermal delivery (Groups 2 and 3) of sCT in pigs. As shown in FIG. 18, the two transdermal groups achieved higher maximal concentration (Cmax) of sCT than the SC group. However, while the Cmax in the SC group was reached 30 min after injection, the Cmax values in the transdermal groups treated with 200 µg sCT or 400 µg sCT were reached after 75 min and 90 min, respectively.

Table 7 summarizes the Cmax values, the area under the curve (AUC) and the bioavailability of sCT in these three groups. As seen in the Table, the AUC of sCT in the transdermal groups was higher than that of the SC group. However, the bioavailability of sCT was 10% and 8% for the transdermal groups treated with 200 µg or 400 µg sCT, respectively, as compared to the SC group, the bioavailability of the later is considered as 100% (Table 7).

patches yielded a ~20% decrease in $Ca^{++}$ concentrations, regardless of sCT dose. Thus, sCT delivered transdermally remained intact and biologically active.

Example 11

Transdermal Delivery of Human Parathyroid Hormone (hPTH 1-34)

The aim of this study was to compare the bioavailability of human parathyroid hormone (hPTH) (1-34) applied transdermally in printed patches to the bioavailability of the hormone injected subcutaneously.

FORTEO® [Teriparatide, hPTH (1-34)] was purchased from Ely Lilly (Indianapolis, Ind., USA).

Pigs (males, 10-12 kg, Large white) were treated as follows:

Group 1: 10 µg of hPTH (1-34) were injected subcutaneously (S.C.; total 3 pigs)

Group 2: Each pig underwent 2 ViaDerm applications at one site on the back. Printed patches containing 50 µg hPTH (1-34) were placed over the treated area and covered with Tegaderm (3M Health Care, St. Paul, Minn.). Total delivery area=1.4 cm$^2$ (total 3 pigs).

Group 3: Each pig underwent 2 ViaDerm applications at one site on the back. Printed patches containing 100 µg hPTH (1-34) were placed over the treated area and covered with Tegaderm. Total delivery area=1.4 cm$^2$ (total 3 pigs).

Group 4: Each pig underwent 2 ViaDerm applications at one site on the back. Printed patches containing 200 µg hPTH (1-34) were placed over the treated area and covered with Tegaderm. Total delivery area=1.4 cm$^2$ (total 3 pigs).

hPTH (1-34) was dissolved in water and then printed on the patches. hPTH (1-34) concentrations in pig plasma were measured by an ELISA kit (Immutopics, San Clemente, Calif., USA).

Figure 20:
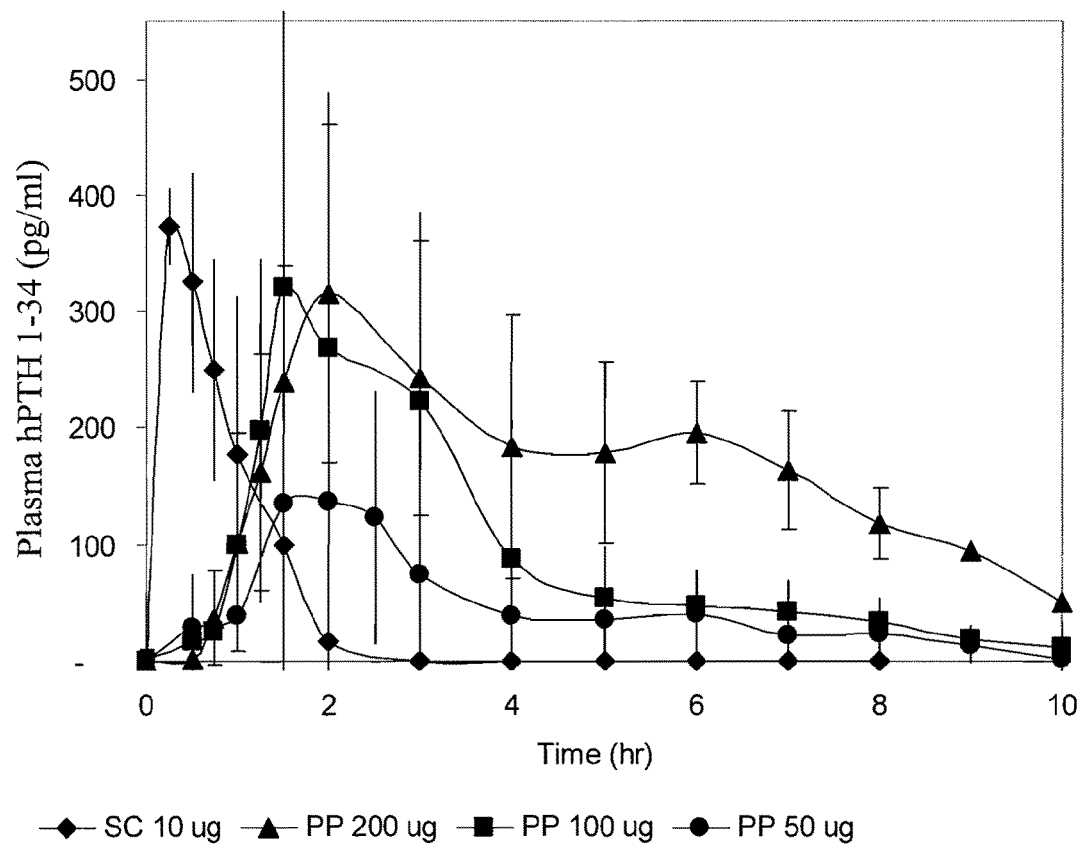
FIG. 20 shows the concentration of plasma human parathyroid hormone (h-PTH) (1-34) in pigs after subcutaneous injection or transdermal delivery of the hormone. hPTH (1-34)-printed patches containing 50, 100 or 200 µg of the hormone were applied on ViaDerm treated skin of pigs and the concentration of immunoreactive plasma hPTH (1-34) as a function of time was measured. As a control, pigs were injected subcutaneously with hPTH (1-34) and the concentration of immunoreactive plasma hPTH (1-34) was measured.

FIG. 20 shows plasma concentrations of hPTH (1-34) after subcutaneous injection or transdermal delivery of the hormone as detailed herein above. As seen in FIG. 20, hPTH (1-34) was efficiently delivered from the printed patches through the micro-channels generated by ViaDerm to the plasma of the treated pigs. Maximal plasma concentration of hPTH (1-34) was ~150 pg/ml when the hormone was delivered transdermally from printed patches containing 50 µg

TABLE 7

Pharmacokinetic parameters for sCT delivery in pigs.

| Treatment | Settings | Delivery area | Delivery site | Cmax (pg/ml) | AUC (pg-min/ml) | bio-availability (%) | Amount delivered (µg) |
|---|---|---|---|---|---|---|---|
| S.C 16.7 µg | | | neck | 2214 ± 1125 | 206,377 ± 63,647 | | |
| Printed patch 400 µg | 290 V 9000 usec 80 µm array | 1.4 | back | 2818 ± 1744 | 390,652 ± 257,031 | 7.98 | 31.92 |
| Printed patch 200 µg | 290 V 9000 usec 80 µm array | 1.4 | back | 2327 ± 673 | 245,988 ± 90,561 | 10.06 | 20.12 |

Figure 19:
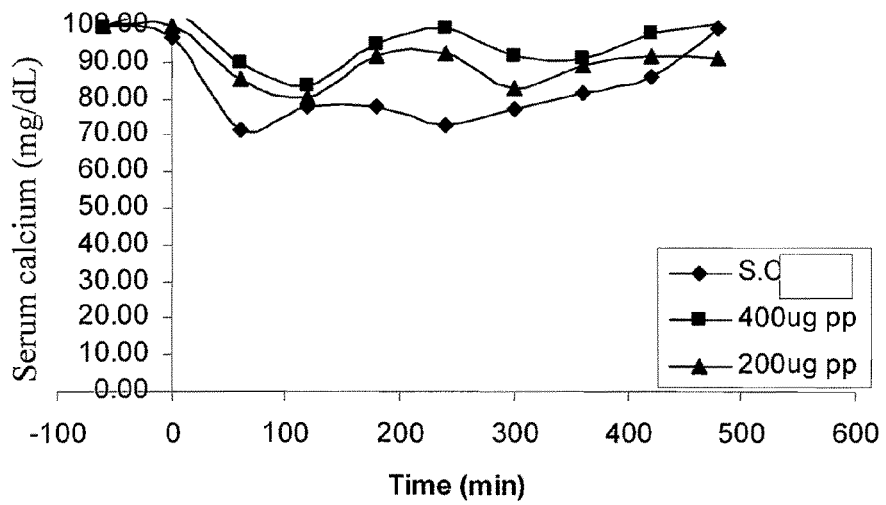
FIG. 19 shows the concentration of calcium in pigs after subcutaneous injection or transdermal delivery of sCT. sCT-printed patches containing 200 or 400 µg sCT were applied on ViaDerm treated skin of pigs and the concentration of plasma calcium as a function of time was measured. As a control, pigs were injected subcutaneously with sCT and the concentration of plasma calcium was measured.

In vivo bioactivity of sCT was evaluated by measuring plasma $Ca^{++}$ concentrations. Reduction in $Ca^{++}$ concentrations in plasma indicates that sCT delivered remains intact and biologically active. As shown in FIG. 19, after SC administration, plasma $Ca^{++}$ concentrations decreased by ~25% from time 0. Transdermal administration from the printed hPTH (1-34), and ~320 pg/ml when the hormone was delivered transdermally from printed patches containing 200 µg hPTH (1-34).

Table 8 summarizes the Cmax values, the area under the curve (AUC) and the bioavailability of hPTH (1-34) in the four treated groups. As seen in Table 8, the bioavailability obtained in pigs treated with ViaDerm and then subjected to 50, 100 or 200 μg hPTH (1-34)-printed patches was 25.2%, 25.2% and 21.9%, respectively, as compared to the bioavailability obtained in the subcutaneous injected group.

hPTH (1-34) printed patch was placed over the application area and covered with Tegaderm. Total delivery area=1.4 cm² (total 3 pigs). Formulation: hPTH (1-34): Trehalose (1:11) in 0.4% citric acid, pH=4.

TABLE 8

Pharmacokinetic parameters for the delivery of hPTH (1-34) formulated in water into pigs.

| hPTH (1-34) administration | Settings | Delivery area (cm²) | Delivery site | Cmax (pg/ml) | AUC (pg · min/ml/) | % bioavailability cf. to S.C. | Amount delivered (μg) |
|---|---|---|---|---|---|---|---|
| S.C. 10 μg | — | — | neck | 374 | 365 | 100 | 10 |
| printed patch 50 μg | 290 V 9000 usec 80 μm array | 1.4 | back | 136 | 460 | 25.2 | 12.6 |
| printed patch 100 μg | 290 V 9000 usec 80 μm array | 1.4 | back | 320 | 919 | 25.2 | 225.18 |
| printed patch 200 μg | 290 V 9000 usec 80 μm array | 1.4 | back | 317 | 1600 | 21.9 | 43.84 |

These results indicate that hPTH (1-34) was efficiently delivered transdermally through the ViaDerm-generated micro-channels.

Example 12

Transdermal Delivery of Human Parathyroid Hormone (hPTH 1-34) in Different Formulations The aim of this experiment was to examine transdermal delivery of different formulations of hPTH (1-34) to pigs.

FORTEO® [Teriparatide, hPTH (1-34)] was purchased from Ely Lilly (Indianapolis, Ind., USA).

The experiment was performed as follows:

Group 1: Each pig underwent two ViaDerm applications (150 micro-channels/cm²) on one site on the back. A 100 μg hPTH (1-34) printed patch was placed over the application area and covered with Tegaderm. Total delivery area=1.4 cm² (total 3 pigs). Formulation: hPTH (1-34) in water for injection (WFI), pH=6.

Group 2: Each pig underwent two ViaDerm applications (150 micro-channels/cm²) on one site on the back. A 100 μg hPTH (1-34) printed patch was placed over the application area and covered with Tegaderm. Total delivery area=1.4 cm² (total 3 pigs). Formulation: hPTH (1-34): Sucrose (1:5.5) in 0.72% acetic acid, pH=4.

Group 3: Each pig underwent two ViaDerm applications (150 micro-channels/cm²) on one site on the back. A 100 μg Group 4: Each pig was injected SC with 0.2 ml (20 μg) of hPTH (1-34) diluted to a 100 μg/ml solution with saline (total 3 pigs).

Figure 21:
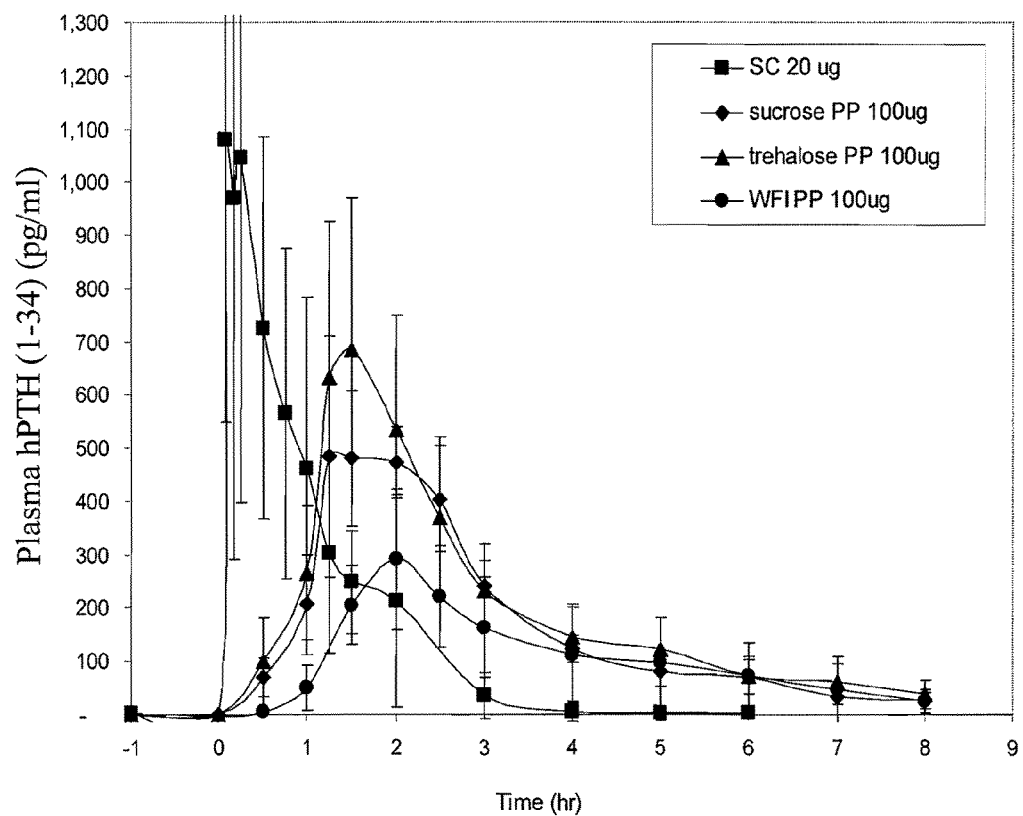
FIG. 21 shows the concentration of plasma human parathyroid hormone (h-PTH) (1-34) in pigs after subcutaneous injection or transdermal delivery of the hormone. hPTH (1-34)-printed patches containing 100 µg of the hormone formulated in either water or in sucrose or trehalose formulations were applied on ViaDerm treated skin of pigs and the concentration of immunoreactive plasma hPTH (1-34) as a function of time was measured. As a control, pigs were injected subcutaneously with hPTH (1-34) and the concentration of immunoreactive plasma hPTH (1-34) was measured.

FIG. 21 shows plasma concentrations of hPTH (1-34) after subcutaneous injection or transdermal delivery of the hormone dissolved in three different formulations as detailed herein above. As seen in FIG. 21, subcutaneous injection of hPTH (1-34) resulted in a rapid elevation of the hormone plasma concentrations with maximal concentration (Cmax) reached 5 to 15 min post-injection. The rapid elevation was followed by rapid elimination of the hormone from plasma (FIG. 21). Transdermal delivery of hPTH (1-34) formulated in water (WFI) exhibited a typical profile of transdermal administration with Cmax values (290.2 pg/ml) reached two hours after hPTH (1-34) administration, followed by gradual elimination. Bioavailability in this group was shown to be the lowest (14.6%) out of the three tested formulations (Table 9).

Transdermal delivery of hPTH (1-34) formulated with sucrose also exhibited a typical profile of transdermal administration with Cmax values (~480 pg/ml) reached at about 1.5 hrs after hormonal administration, followed by gradual elimination. Bioavailability in this group was 22.9% and shown to be higher than that obtained for the WFI formulation, but slightly lower than that obtained for the trehalose formulation (Table 91).

Transdermal delivery of hPTH (1-34) formulated with trehalose exhibited typical profile of transdermal administration with Cmax (~684.9 pg/ml) reached at 1.5 hrs after hormonal administration followed by gradual elimination. Bioavailability in this group was shown to be the highest (27.2%) out of the three tested formulations (Table 9).

TABLE 9

Pharmacokinetic parameters for the delivery of hPTH (1-34) formulated in different formulations into pigs.

| Treatment | Settings | Delivery area | Delivery site | Cmax (pg/ml) | AUC (pg-min/ml) | % bio | Amount delivered (μg) |
|---|---|---|---|---|---|---|---|
| S.C. 20 ug | — | — | neck | 1079 | 1164 ± 760.85 | 100 | 20 |
| sucrose printed patch 100 ug | 6750 msec 80 mm array 2 applications/site | 4.9 | back | 483.4 | 1335 ± 107.58 | 22.94 | 22.94 |

TABLE 9-continued

Pharmacokinetic parameters for the delivery of hPTH (1-34) formulated in different formulations into pigs.

| Treatment | Settings | Delivery area | Delivery site | Cmax (pg/ml) | AUC (pg-min/ml) | % bio | Amount delivered (μg) |
|---|---|---|---|---|---|---|---|
| trehalose printed patch 100 ug | 6750 msec 80 mm array 2 applications/site | 4.9 | back | 684.9 | 1584 ± 511.06 | 27.22 | 27.22 |
| WFI PP 100 ug | 6750 msec 80 mm array 2 applications/site | 4.9 | back | 290.2 | 850.67 ± 436.02 | 14.6 | 14.6 |

These results indicate that hPTH (1-34) formulated with trehalose in 0.4% citric acid achieved the highest transdermal delivery as measured by bioavailability parameters and thus is preferable for use in human.

Example 13

Transdermal Delivery of hPTH (1-34) to Humans

Transdermal drug delivery study of hPTH (1-34) in four female adult healthy human volunteers was performed using ViaDerm and printed patches.

To evaluate the transdermal delivery of hPTH (1-34), printed patches containing 100 μg or 200 μg hPTH (1-34) (FORTEO®, Teriparatide purchased from Ely Lilly, Indianapolis, Ind., USA) were prepared. Patch area was 1.44 $cm^2$ ViaDerm parameters: electrode array of 75 or 100 micro-channels/$cm^2$; ViaDerm was applied two or three times generating micro-channels at a density of 150 or 300 micro-channels/$cm^2$; Voltage: 290 volts, constant voltage; Burst length: 5000 μsec; Maximal current: 50 mA.

Each female adult received five treatments of hPTH (1-34) with a minimum of 2 day clearance between treatments. The treatments were as follows:
1. Three ViaDerm applications (final density of 300 micro-channels/$cm^2$) on one site of the upper arm. Two printed patches, each containing 100 μg hPTH (1-34), were placed over the application area (each for 6 hours).
2. Two ViaDerm applications (final density of 150 micro-channels/$cm^2$) on one site of the upper arm. Two printed patches, each containing 200 μg hPTH (1-34), were placed over the application area.
3. Three ViaDerm applications (final density of 300 micro-channels/$cm^2$) on one site of the upper arm. Two printed patches, each containing 200 μg hPTH (1-34), were placed over the application area.
4. Subcutaneous (SC) injection of 20 μg hPTH (1-34) (FORTEO® [Teriparatide was purchased from Ely Lilly, Indianapolis, Ind., USA).
5. SC injection of 60 μg hPTH (1-34) (FORTEO®).

Plasma hPTH (1-34), calcium ions and phosphate ions were determined by Elisa using commercial kits.

Figure 22A:
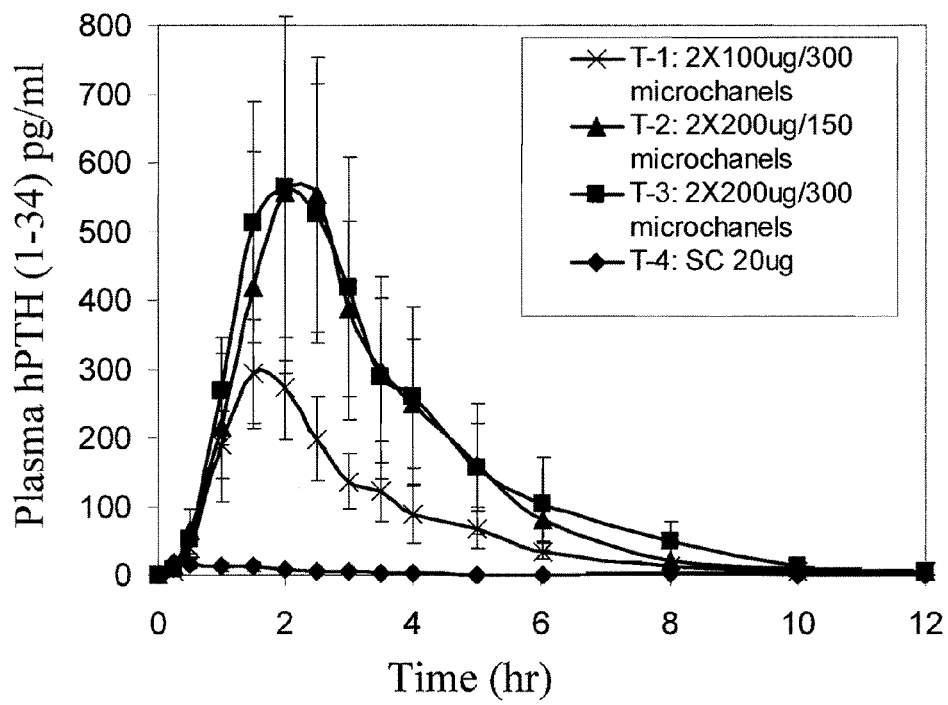
FIGS. 22A and B show average plasma concentrations of hPTH (1-34) in four women after transdermal administration of the hormone using ViaDerm treatment followed by application of hPTH (1-34)-printed patches. As a control, subcutaneous administration of hPTH (1-34) was determined.
Figure 22B:
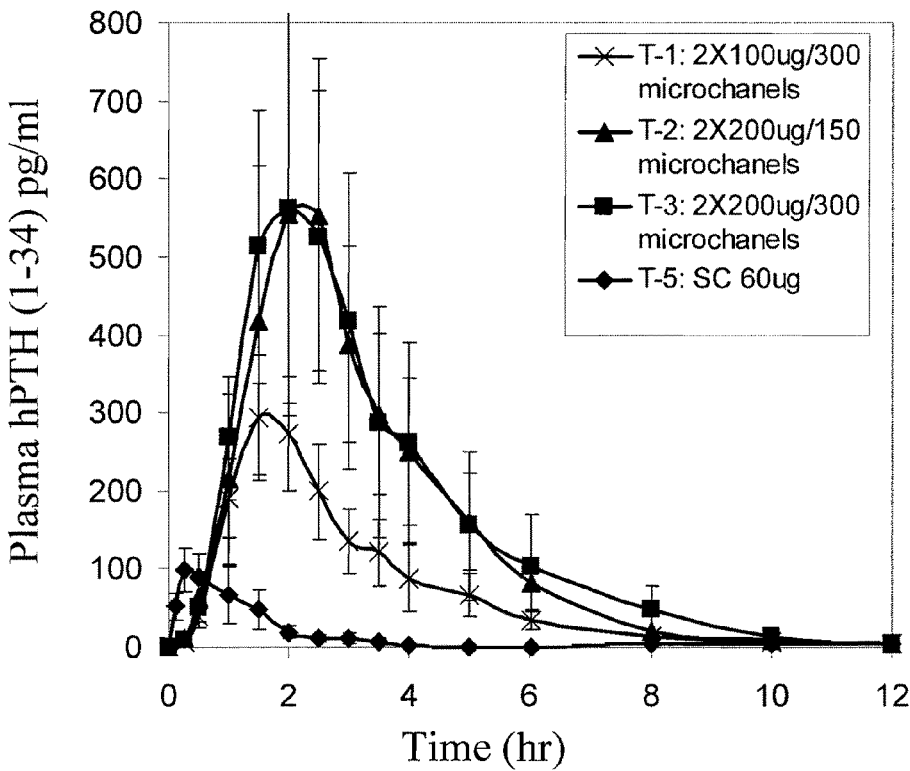

FIG. 22 shows plasma hPTH (1-34) concentrations in each of the treatments. As shown in FIG. 22, generating micro-channels in human skin at a density of 150 or 300 micro-channels/$cm^2$ and applying two printed patches, each containing 200 μg, where micro-channels were present, resulted in higher plasma hPTH (1-34) concentrations compared to the hPTH (1-34) concentrations obtained when the density of the generated micro-channels was 300 micro-channels/$cm^2$ and the printed patches contained only 100 μg of hPTH (1-34).

Table 10 summarizes the individual values for each adult female. As shown in Table 10, for treatment #1, i.e., 300 micro-channels/$cm^2$ and 2 printed patches, each containing 100 μg of hPTH (1-34), a mean peak plasma concentration (Cmax) of 331 (pg/ml) was reached at time (Tmax) of 1.5 hr.

For treatment #2, i.e., 150 micro-channels/$cm^2$ and 2 printed patches, each containing 200 μg of hPTH (1-34), a mean peak plasma concentration (Cmax) of 642 (pg/ml) was reached at time (Tmax) of 2.1 hr.

For treatment #3, i.e., 300 micro-channels/$cm^2$ and 2 printed patches, each containing 200 μg of hPTH (1-34), a mean peak plasma concentration (Cmax) of 651.34 (pg/ml) was reached at time (Tmax) of 2.0 hr.

For treatments #4 and #5, i.e., SC administration of 20 or 60 μg of hPTH (1-34), a mean peak plasma concentration (Cmax) of 22 (pg/ml) and 115 (pg/ml) was reached at time (Tmax) of 1.8 and 0.8 h, respectively.

Figure 23:
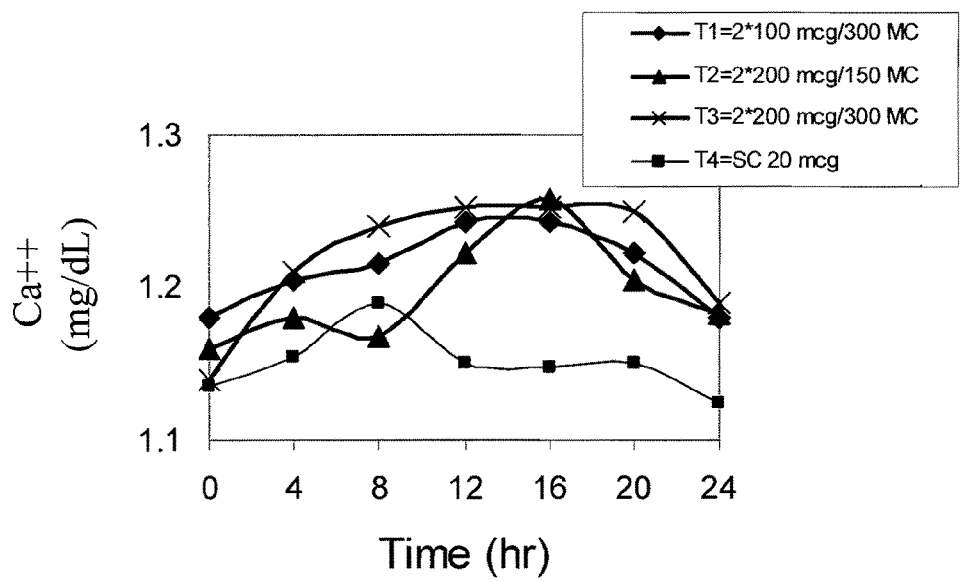
FIG. 23 shows average plasma concentration of calcium ions in four women after transdermal administration of hPTH (1-34) using ViaDerm treatment followed by application of hPTH (1-34)-printed patches. As a control, subcutaneous administration of hPTH (1-34) was determined.
Figure 24:
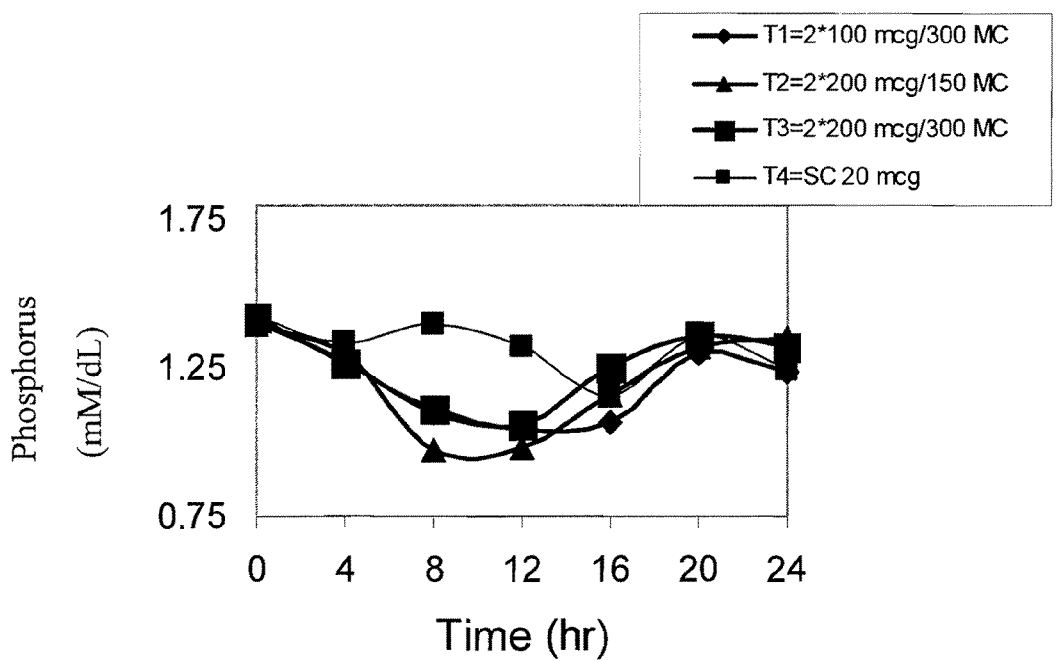
FIG. 24 shows average plasma concentration of phosphorous in four women after transdermal administration of hPTH (1-34) using ViaDerm treatment followed by application of hPTH (1-34)-printed patches. As a control, subcutaneous administration of hPTH (1-34) was determined.

FIG. 23 shows plasma concentrations of calcium ions and FIG. 24 shows plasma concentrations of phosphorus. As shown in FIGS. 23 and 24, the elevation of calcium ions and the decrease of phosphorous were evident for all transdermal and SC treatments, indicating that hPTH (1-34) delivered to the blood was active.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

TABLE 3

Stability of rhGH-printed patches.

| | (−)18° C. | | 4° C. | | RT | |
|---|---|---|---|---|---|---|
| Time | Impurities/ Degradation products by RF HPLC | Agreggates and dimmers by SE HPLC | Impurities/ Degradation products by RF HPLC | Agreggates and dimmers by SE HPLC | Impurities/ Degradation products by RF HPLC | Agreggates and dimmers by SE HPLC |
| Initial | NA | 0.4 | NA | 0.4 | NA | 0.4 |
| 1 month | 1.2 | NP | 1.1 | NP | 1.2 | 1.8 |
| 2 months | 0.9 | 0.2 | 1.2 | 0.4 | 1.1 | 3.1 |
| 3 months | 1.2 | 0.1 | 3.4 | 0.5 | 3.5 | 3.3 |

Amount of rhGH applied on each patch was 200 µg.

The values correspond to % of peak area.

RP = Reversed Phase;

SE = Size Exclusion;

NA = Not Applicable;

NP = Not Performed

TABLE 4

Stability of rhGH-printed patches.

| | (−)18° C. | | 4° C. | | RT | |
|---|---|---|---|---|---|---|
| Time | Impurities/ Degradation products by RF HPLC | Agreggates and dimmers by SE HPLC | Impurities/ Degradation products by RF HPLC | Agreggates and dimmers by SE HPLC | Impurities/ Degradation products by RF HPLC | Agreggates and dimmers by SE HPLC |
| Initial | NA | 0.4 | NA | 0.4 | NA | 0.4 |
| 1 month | 1.2 | NP | 1.1 | NP | 1.2 | 1.8 |
| 2 months | 0.9 | 0.2 | 1.2 | 0.4 | 1.1 | 3.1 |
| 3 months | 1.2 | 0.1 | 3.4 | 0.5 | 3.5 | 3.3 |

Amount of rhGH applied on each patch was 200 µg.
The values correspond to % of peak area.
The stability was determined after 3 months.

TABLE 10

Delivery of hPTH (1-34) in female adults

| | Treatment | Subject | Dose (ug) | Cmax | | | Tmax | | | AUC | | |
|---|---|---|---|---|---|---|---|---|---|---|---|---|
| | | | | Cmax | AVG | SD | Tmax | AVG | SD | AUC | AVG | SD |
| 12 h | T-1 | 1 | 200 | 94.366 | 330.918 | 158.939 | 1.0 | 1.5 | 0.4 | 346 | 962.5 | 428.8 |
| | | 2 | 200 | 394.054 | | | 2.0 | | | 1340 | | |
| | | 3 | 200 | 437.693 | | | 1.5 | | | 1097 | | |
| | | 4 | 200 | 397.560 | | | 1.5 | | | 1067 | | |
| | T-2 | 1 | 400 | 72.528 | 642.299 | 513.126 | 1.5 | 2.1 | 0.5 | 398 | 1941.8 | 1397.5 |
| | | 2 | 400 | 463.893 | | | 2.5 | | | 1498 | | |
| | | 3 | 400 | 1293.464 | | | 2.0 | | | 3743 | | |
| | | 4 | 400 | 739.311 | | | 2.5 | | | 2128 | | |
| | T-3 | 1 | 400 | 296.887 | 651.347 | 446.648 | 2.5 | 2.0 | 0.4 | 886 | 2028.3 | 1757.7 |
| | | 2 | 400 | 534.872 | | | 1.5 | | | 1251 | | |
| | | 3 | 400 | 1304.179 | | | 2.0 | | | 4649 | | |
| | | 4 | 400 | 469.450 | | | 2.0 | | | 1327 | | |
| | T-4 | 1 | 20 | 12.196 | 29.291 | 12.076 | 6.0 | 1.8 | 2.8 | 103 | 152.3 | 33.7 |
| | | 2 | 20 | 37.556 | | | 0.3 | | | 172 | | |
| | | 3 | 20 | 29.350 | | | 0.3 | | | 158 | | |
| | | 4 | 20 | 38.062 | | | 0.5 | | | 176 | | |
| | T-5 | 1 | 60 | 59.209 | 111.514 | 59.903 | 1.0 | 0.8 | 0.3 | 84 | 264.3 | 201.3 |
| | | 2 | 60 | 66.482 | | | 0.5 | | | 100 | | |
| | | 3 | 60 | 185.324 | | | 0.5 | | | 474 | | |
| | | 4 | 60 | 135.040 | | | 1.0 | | | 399 | | |

What is claimed is:

1. A printed patch comprising a non-adhesive liner and a dried pharmaceutical composition comprising a calcitonin present on the non-adhesive liner, wherein the non-adhesive liner is made of a material that is not permeable to the calcitonin.

2. The printed patch according to claim 1, wherein the calcitonin is selected from the group consisting of salmon calcitonin, eel calcitonin, human calcitonin, rat calcitonin, sheep calcitonin, chicken calcitonin, ox calcitonin, and pig calcitonin.

3. The printed patch according to claim 2, wherein the salmon calcitonin is selected from the group consisting of salmon calcitonin I as set forth in SEQ ID NO:1, salmon calcitonin II as set forth in SEQ ID NO:2, salmon calcitonin III as set forth in SEQ ID NO:3, salmon calcitonin IV as set forth in SEQ ID NO:4, and salmon calcitonin V as set forth in SEQ ID NO:5.

4. A printed patch comprising a non-adhesive liner and a dried pharmaceutical composition comprising a salmon calcitonin present on the non-adhesive liner and a stabilizer, wherein the salmon calcitonin is salmon calcitonin I as set forth in SEQ ID NO:1, the stabilizer is trehalose, and the non-adhesive liner is made of a material that is not permeable to the calcitonin.

5. The printed patch according to claim 1, wherein the pharmaceutical composition further comprises a stabilizer.

6. The printed patch according to claim 5, wherein the stabilizer is a simple or complex carbohydrate.

7. The printed patch according to claim 6, wherein the simple or complex carbohydrate is selected from the group consisting of mannose, glucose, galactose, raffinose, cellobiose, gentiobiose, sucrose and trehalose.

8. The printed patch according to claim 1, wherein the pharmaceutical composition further comprises a buffering agent.

9. A method for treating a bone or cartilage disease or disorder in a subject comprising:
    (a) generating a plurality of micro-channels in an area of the skin of a subject;
    (b) affixing a printed patch according to claim 1 to the area of the skin of the subject where the plurality of micro-channels are present, the printed patch comprises a therapeutically effective amount of a calcitonin, thereby treating the bone or cartilage disease or disorder.

10. The method according to claim 9, wherein the calcitonin is selected from the group consisting of salmon calcitonin, eel calcitonin, human calcitonin, rat calcitonin, sheep calcitonin, chicken calcitonin, ox calcitonin, and pig calcitonin.

11. The method according to claim 10, wherein the salmon calcitonin is selected from the group consisting of salmon calcitonin I as set forth in SEQ ID NO:1, salmon calcitonin II as set forth in SEQ ID NO:2, salmon calcitonin III as set forth in SEQ ID NO:3, salmon calcitonin IV as set forth in SEQ ID NO:4, and salmon calcitonin V as set forth in SEQ ID NO:5.

12. The method according to claim 11, wherein the salmon calcitonin is salmon calcitonin I as set forth in SEQ ID NO:1.

13. The method according to claim 9, wherein the pharmaceutical composition further comprises a stabilizer.

14. The method according to claim 13, wherein the stabilizer is a simple or complex carbohydrate.

15. The method according to claim 14, wherein the simple or complex carbohydrate is selected from the group consisting of mannose, glucose, galactose, raffinose, cellobiose, gentiobiose, sucrose and trehalose.

16. The method according to claim 9, wherein the pharmaceutical composition further comprises a buffering agent.

17. The method according to claim 9, wherein the bone disease or disorder is selected from the group consisting of osteopenia and osteoporosis; hypercalcemia; Paget's disease; bone fracture, both vertebral and non-vertebral or bone deficiency; Sudeck's disease; primary or secondary hyperparathyroidism; periodontal disease or defect; metastatic bone disorder; osteolytic bone disease; post-plastic bone surgery; post-dental implantation; and renal osteodystrophy.

18. The method according to claim 17, wherein the bone disease is osteoporosis.

19. The method according to claim 9, wherein the cartilage disease or disorder is selected from the group consisting of osteoarthritis; rheumatoid arthritis; septic arthritis; post-prosthetic joint surgery; and degenerative cartilage loss following traumatic joint injury.

20. The method according to claim 19, wherein the disease is osteoarthritis.

21. The method according to claim 9, wherein the subject is a human.

22. The method according to claim 19, wherein the area of the skin of the subject is adjacent to an affected or injured joint.

* * * * *

SEQUENCE LISTING

<160> NUMBER OF SEQ ID NOS: 5

<210> SEQ ID NO 1
<211> LENGTH: 32
<212> TYPE: PRT
<213> ORGANISM: Oncorhynchus mykiss

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 32
<212> TYPE: PRT
<213> ORGANISM: Oncorhynchus nerka

<400> SEQUENCE: 2

Cys Ser Asn Leu Ser Thr Cys Val Leu Gly Lys Leu Ser Gln Asp Leu
1               5                   10                  15

His Lys Leu Gln Thr Phe Pro Arg Thr Asn Thr Gly Ala Gly Val Pro
            20                  25                  30

<210> SEQ ID NO 3
<211> LENGTH: 32
<212> TYPE: PRT
<213> ORGANISM: Oncorhynchus

<400> SEQUENCE: 3

Cys Ser Asn Leu Ser Thr Cys Met Leu Gly Lys Leu Ser Gln Asp Leu
1               5                   10                  15

His Lys Leu Gln Thr Phe Pro Arg Thr Asn Thr Gly Ala Gly Val Pro
            20                  25                  30

<210> SEQ ID NO 4
<211> LENGTH: 32
<212> TYPE: PRT
<213> ORGANISM: Oncorhynchus gorbuscha

<400> SEQUENCE: 4

Cys Ser Asn Leu Ser Thr Cys Val Leu Gly Lys Leu Ser Gln Asp Leu
1               5                   10                  15

His Lys Leu Gln Thr Phe Pro Arg Thr Asp Val Gly Ala Gly Thr Pro
            20                  25                  30

<210> SEQ ID NO 5
<211> LENGTH: 32
<212> TYPE: PRT
<213> ORGANISM: Oncorhynchus mykiss

<400> SEQUENCE: 5

Cys Ser Asn Leu Ser Thr Cys Met Leu Gly Lys Leu Ser Gln Asp Leu
1               5                   10                  15

His Lys Leu Gln Thr Phe Pro Arg Thr Asp Val Gly Ala Gly Thr Pro
            20                  25                  30